(12) United States Patent
Sznaidman

(10) Patent No.: US 6,870,048 B2
(45) Date of Patent: Mar. 22, 2005

(54) PROCESS FOR THE PREPARATION OF 2'-HALO-β-L-ARABINOFURANOSYL NUCLEOSIDES

(75) Inventor: Marcos Sznaidman, Durham, NC (US)

(73) Assignee: Triangle Pharmaceuticals, Durham, NC (US)

(*) Notice: Subject to any disclaimer, the term of this patent is extended or adjusted under 35 U.S.C. 154(b) by 0 days.

(21) Appl. No.: 10/112,403

(22) Filed: Mar. 29, 2002

(65) Prior Publication Data

US 2003/0060622 A1 Mar. 27, 2003

Related U.S. Application Data

(60) Provisional application No. 60/280,307, filed on Mar. 30, 2001.

(51) Int. Cl.[7] .......................... C07H 19/19; C07H 19/06
(52) U.S. Cl. .................. 536/27.4; 536/28.5; 536/28.51; 536/28.52; 536/28.53; 536/28.54; 536/28.1; 536/25.3; 536/25.31
(58) Field of Search ............................. 536/27.4, 28.5, 536/28.51, 28.52, 28.53, 28.54, 28.1, 25.3, 25.31

(56) References Cited

U.S. PATENT DOCUMENTS

| | | |
|---|---|---|
| 5,565,438 A | 10/1996 | Chu et al. |
| 5,567,688 A | 10/1996 | Chu et al. |
| 5,587,362 A | 12/1996 | Chu et al. |
| 5,808,040 A | 9/1998 | Chu et al. |

FOREIGN PATENT DOCUMENTS

WO    WO 95/20595 A1    3/1995

OTHER PUBLICATIONS

Sznaidman, M. L., *Nucleosides, Nucleotides & Nucleic Acids,* 2002, 21(2), 155–163.

Albert, M., et al. "A Novel Direct Route to 2–Deoxy–2–fluoro–aldoses and their Corresponding Derivatives." *Tetrahedron.* 54:4839–4848, 1998.

Balog, A., et al. "A Practical Asymmetric Synthesis of a Pseudomonic Acid Precursor from D–Arabinose or D–Xylose." *Synthetic Comm.* 26(5):935–944, 1996.

Bols, M., et al. "Preparation of 2,3–Epoxyaldonolactones and their Conversion into 2–Fluoro–2–deoxy–aldonolactones and –sugars." *Acta Chem. Scand.* 44(3):252–256, 1990.

Chu, C.K., et al. "Use of 2'–Fluoro–5–Methyl–B–L–Arabinofuranosyluracil as a Novel Antiviral Agents for Hepatitis B Virus and Epstein–Barr Virus." *Antimicrobial Agents Chemother.* 39(4):979–981, Apr. 1995.

Du, J., et al. "A Practical Synthesis of L–FMAU From L–Arabinose." *Nucleosides & Nucleosides.* 18(2):187–195, 1999.

Fristad, W.E., et al. "Conversion of Alkenes to 1,2–Diazides and 1,2–Diamines." *J. Org. Chem.* 50:3647–3649, 1985.

Ma, T., et al. "Structure–Activity Relationships of 1–(2–Deoxy–2–fluoro–β–L–aradinofuranosyl)pyrimidine Nucleosides as Anti–Hepatitis B Virus Agents." *J. Med. Chem.* 39(14):2835–2843, 1996.

Ryan, K.J., et al. "[55] 9–B–L–Ribofuranosyladenine ('L–Adenosine'): Configurational Inversion within a Furanoid Ring." *Synthetic Procedures in Nucleic Acid Chemistry VI.* 163–167.

Smiatacz, Z., et al. "Configuration and Conformation of the Products of Reaction of 3,4–Di–O–Acetyl–2–Deoxy–2–Nitroso–B–D–Arabinopyranosyl Chloride with Pyrazole." *Carbohydr. Res.* 172:171–182, 1988.

Wright, J.A., et al. "Nucleosides. LX[1A] Fluorocarbohydrates. XXII. [1b] Synthesis of 2–Deoxy–2–fluoro–D–arabinose and 9–(2–Deoxy–2–fluoro–α–and –β–D–arabinofuranosyl)adenines[2]" *J. Org. Chem.* 34(9):2632–2636, Sep. 1969.

*Primary Examiner*—James O Wilson
*Assistant Examiner*—Howard V. Owens, Jr.
(74) *Attorney, Agent, or Firm*—Sherry M. Knowles, Esq.; King & Spalding, LLP

(57) ABSTRACT

The present invention is directed to the process for the preparation of 2'-deoxy-2'-halo-β-L-arabinofuranosyl nucleosides, and in particular, 2'-deoxy-2'-fluoro-β-L-arabinofuranosyl thymine (L-FMAU), from L-arabinose, which is commercially available and less expensive than L-ribose or L-xylose, in ten steps. All of the reagents and starting materials are inexpensive and no special equipment is required to carry out the reactions.

11 Claims, 1 Drawing Sheet

PROCESS FOR THE PREPARATION OF 2'-HALO-β-L-ARABINOFURANOSYL NUCLEOSIDES

This application claims priority to U.S. Provisional Application No. 60/280,307, filed on Mar. 30, 2001.

FIELD OF THE INVENTION

This invention is in the area of the synthesis of 2'-deoxy-2'-halo-β-L-arabinofuranosyl nucleosides, and is specifically directed to an efficient method of synthesis and manufacturing of 1-(2'-deoxy-2'-fluoro-β-L-arabinofuranosyl)-thymine (L-FMAU).

BACKGROUND OF THE INVENTION

Infection by hepatitis B virus is a problem of enormous dimensions. Hepatitis B virus has reached epidemic levels worldwide. It is estimated that as many as 350 million people worldwide are persistently infected with HBV, many of whom develop associated pathologies such as chronic hepatic insufficiency, cirrhosis, and hepatocellular carcinoma. After a two to three month incubation period in which the host is unaware of the infection, HBV infection can lead to acute hepatitis and liver damage, that causes abdominal pain, jaundice, and elevated blood levels of certain enzymes. About 1–2% of these develop fulminant hepatitis, a rapidly progressive, often fatal form of the disease in which massive sections of the liver are destroyed, with a mortality rate of 60–70%.

The Epstein-Barr virus is a member of the genus Lymphocryptovirus, which belongs to the subfamily gammaherpesvirine. It is notably lymphotropic. EBV has the classic structure of herpes viruses, viz., its double-stranded DNA genome is contained within an icosapentahedral nucleocapsid, which, in turn, is surrounded by a lipid envelope studded with viral glycoproteins. EBV is now recognized as a cause of B-cell lymphoproliferative diseases, and has been linked to a variety of other severe and chronic illnesses, including a rare progressive mononucleosis-like syndrome and oral hairy leukoplakia in AIDS patients. The suggestion that EBV is a major cause of chronic fatigue has not withstood scrutiny. EBV is primarily transmitted through saliva, although some infections are transmitted by blood transfusion. More than 85% of patients in the acute phase of infectious mononucleosis secrete EBV.

It has been discovered that certain L-nucleosides, mirror images of the natural DNA constituents may inhibit DNA synthesis at the triphosphate level probably by tight binding to the viral polymerase in the first stage of viral DNA synthesis.

2'-Deoxy-2'-fluoro-β-L-arabinofuranosyl nucleosides have the general formula:

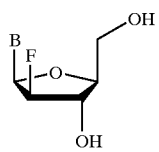

wherein B is a pyrimidine, purine, heterocyclic or heteroaromatic base.

Reported Syntheses of L-FMAU

Yung Chi Cheng, Chung K. Chu and others first reported that 1-(2'-deoxy-2'-fluoro-β-L-arabinofuranosyl)-thymine (L-FMAU) exhibits superior activity against hepatitis B virus and Epstein Barr virus in 1994. See U.S. Pat. Nos. 5,587,362; 5,567,688; 5,565,438 and 5,808,040 and International Patent Application published as WO 95/20595.

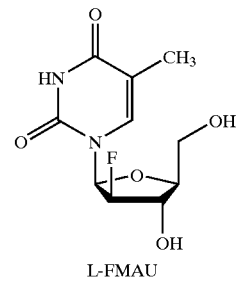

L-FMAU

The Cheng patents describe a synthesis of L-FMAU from the sugar L-xylose (formula A) as well as the sugar L-ribose (formula B).

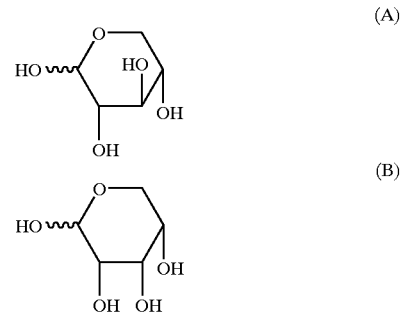

These patents describe the synthesis of L-FMAU from L-xylose via conversion to the key intermediate 1-O-acetyl-2,3,5-tri-O-benzoyl-β-L-ribofuranose (see for example the '688 patent, starting at column 4, line 62). The key intermediate was synthesized from L-xylose in a total yield of 20% (see also L. Vargha, Chem. Ber., 1954, 87, 1351; Holy, A., et al., Synthetic Procedures in Nucleic Acid Chemistry, V1, 163–67). This synthesis was also reported in Ma, T.; Pai, S. B.; Zhu, Y. L; Lin, T. S.; Shanmunganathan, K.; Du, J. F.; Wang, C. G.; Kim, H.; Newton, G. M.; Cheng, Y. C.; Chu, C. K. J. Med. Chem. 1996, 39, 2835. The inversion of the hydroxy group of L-xylose was achieved via the formation of the 5-O-benzoyl-1,2-O-isopropylidene-α-L-ribofuranoside, followed by a stereoselective hydride transfer during the reduction of the cycloketone furanoside with NaBH₄. The resulting ribofuranoside was then converted to 1-O-acetyl-2,3,5-tri-O-benzoyl-β-L-ribofuranose, the key intermediate in the synthesis of L-FMAU (See Scheme A).

Scheme A

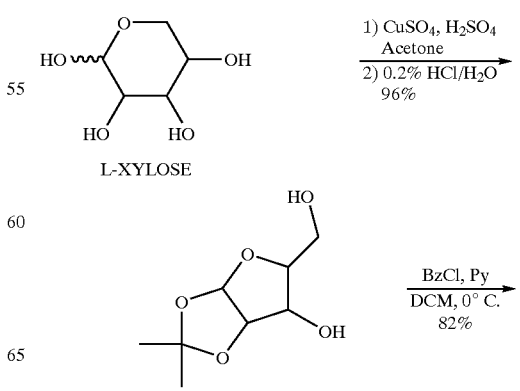

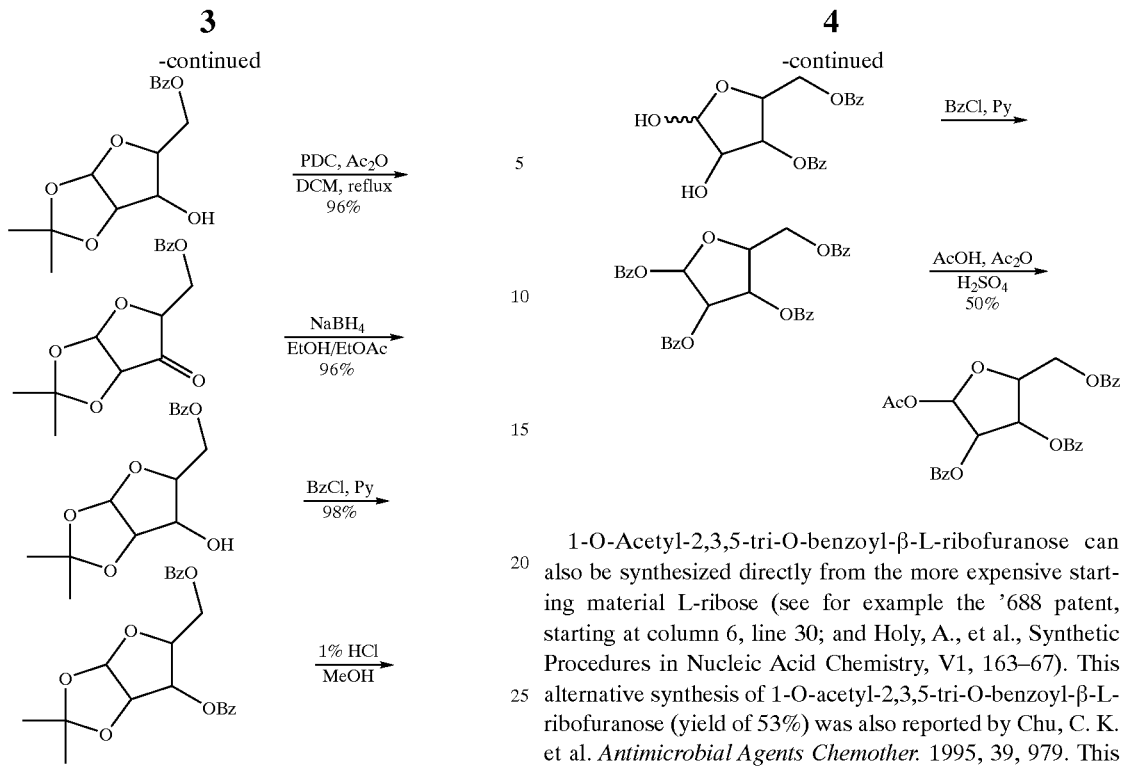

1-O-Acetyl-2,3,5-tri-O-benzoyl-β-L-ribofuranose can also be synthesized directly from the more expensive starting material L-ribose (see for example the '688 patent, starting at column 6, line 30; and Holy, A., et al., Synthetic Procedures in Nucleic Acid Chemistry, V1, 163–67). This alternative synthesis of 1-O-acetyl-2,3,5-tri-O-benzoyl-β-L-ribofuranose (yield of 53%) was also reported by Chu, C. K. et al. *Antimicrobial Agents Chemother.* 1995, 39, 979. This synthetic route to L-FMAU is set out below in Scheme B.

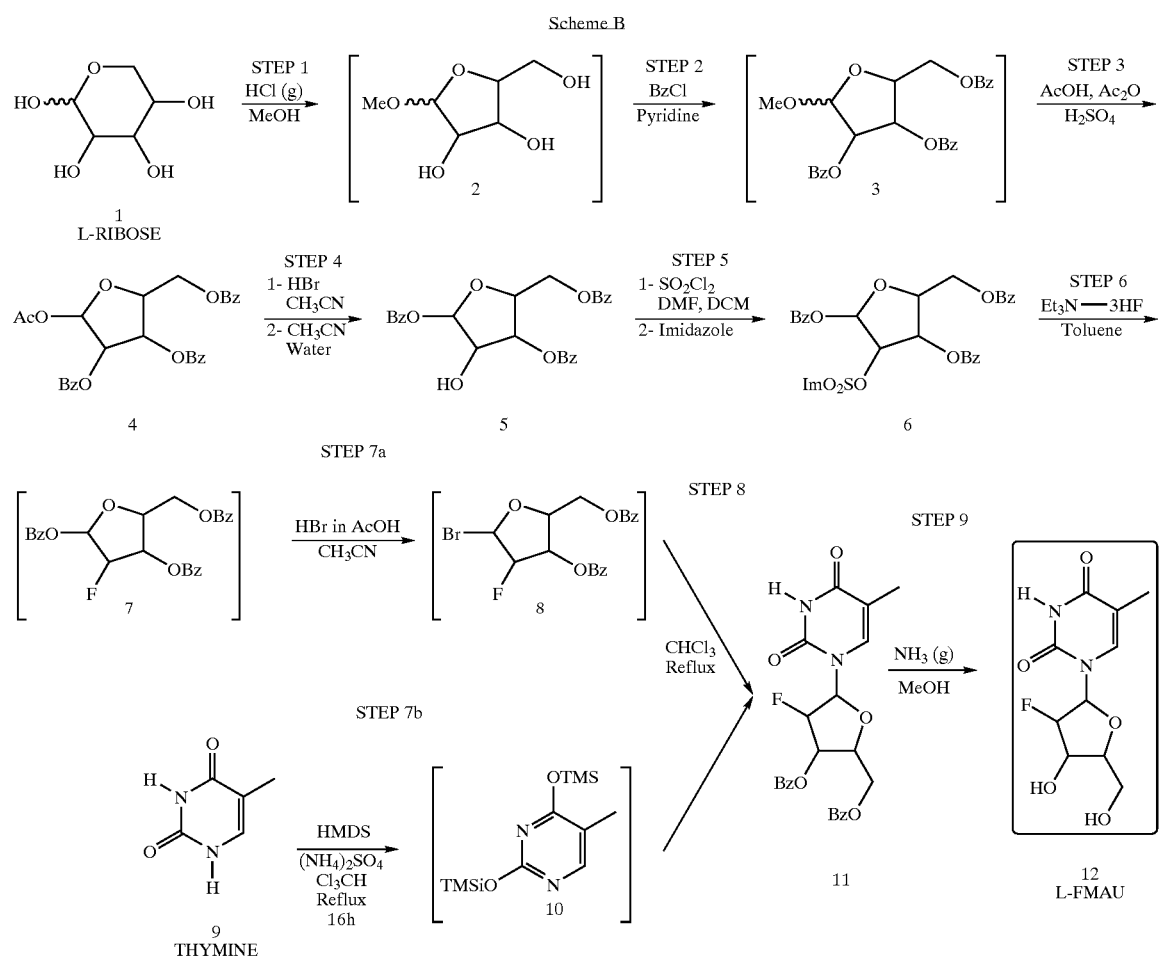

The key intermediate was subsequently fluorinated in a nucleophilic displacement reaction at $C_2$ to obtain 1,3,5-tri-O-benzoyl-2-deoxy-2-fluoro-L-arbinofuranose, which was condensed with a desired base, such as thymine (5-methyluracil) through the bromosugar to provide the 2'-deoxy-2'-fluoro-arabinofuranosyl nucleosides in various yields.

Chu et al. later developed a synthesis for the production of L-FMAU from L-arabinose in 14 steps and an overall yield of 8% (Du, J.; Choi, Y.; Lee, K.; Chun, B. K.; Hong, J. H.; Chu, C. K. *Nucleosides and Nucleosides* 1999, 18, 187). L-Arabinose was converted to L-ribose in 5 steps (Scheme C). L-Ribose was then used in the synthesis 1-O-acetyl-2,3,5-tri-O-benzoyl-β-L-ribofuranose, which as described above led to the formation of L-FMAU.

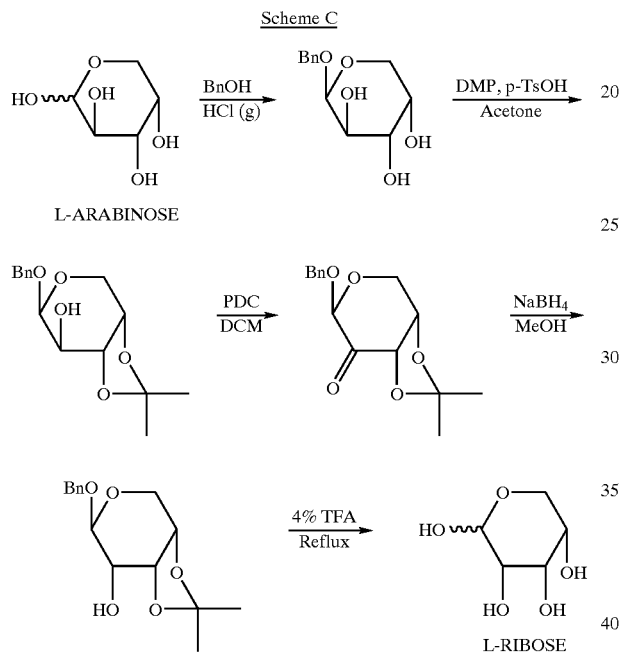

The processes mentioned above either start from an expensive sugar (L-ribose or L-xylose) and/or are very long, with low yields. In addition, they involve the use of a nucleophilic form of fluoride such as $KHF_2$ or $Et_3N$-3HF, which is difficult to handle and requires the displacement of an activated hydroxyl group. The instability of DAST prevents its use on large scale. The conversion of 1-O-acetyl-2,3,5-tri-O-benzoyl-β-L-ribofuranose (TBAR) to 1,3,5-tri-O-benzoyl-β-L-ribofuranose generates 2,3,5-tri-O-benzoyl-β-L-ribofuranose as a side-product, though it can be reconverted to TBAR.

Reported Syntheses of 1-O-methyl-2-deoxy-2-fluoro-arabinofuranoside

The synthesis of 1-O-methyl-2-deoxy-2-fluoro-α-D-arabinofuranoside, has been reported by Wright et al. (Wright, J. A.; Taylor, N. F.; Fox, J. J. *J. Org. Chem* 1969, 34, 2632, and references therein). In this report, D-xylose is used as the starting material, which after a conversion to the corresponding furanose and a series of protection reactions, gave an epoxy furanoside as an intermediate. This compound was further converted to 5-O-benzyl-1-O-methyl-2-deoxy-2-fluoro-α-D-arabinofuranoside, which after removal of the benzyl group afforded 1-O-methyl-2-deoxy-2-fluoro-α-D-arabinofuranoside (Scheme D).

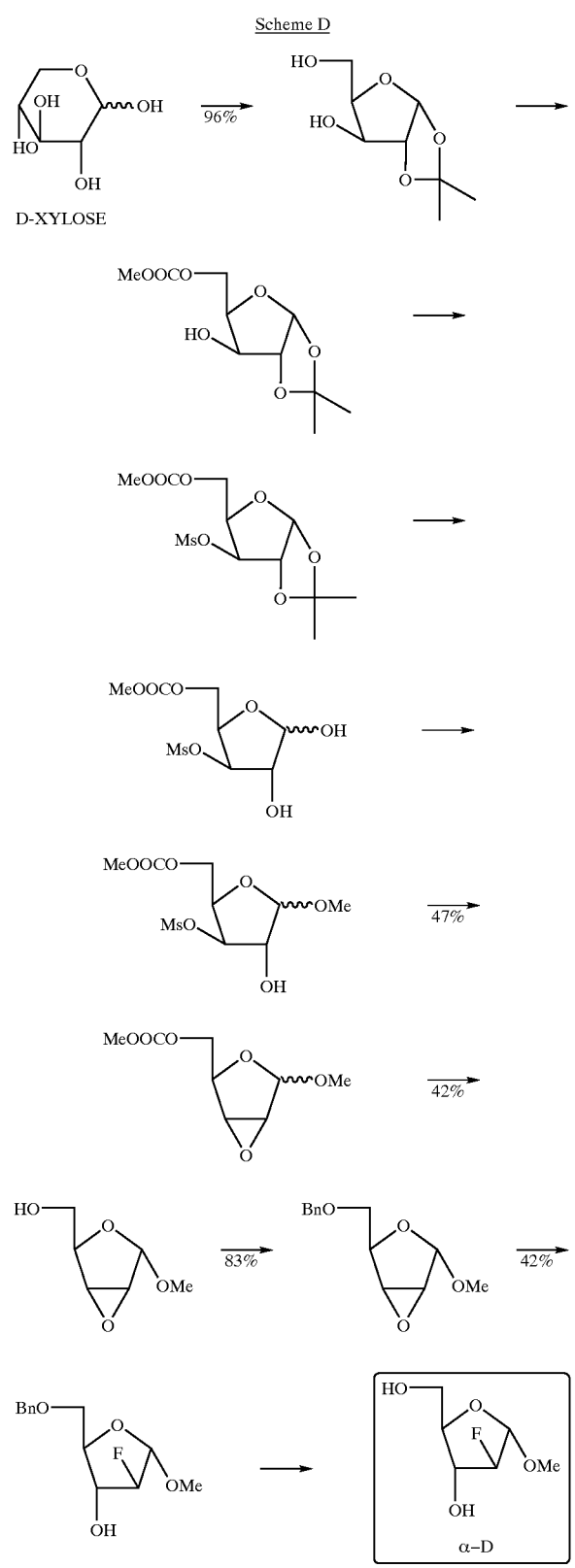

The synthesis of the 1-O-methyl-2-deoxy-2-fluoro-β-D-arabinofuranoside (the anomer of the above compound) was reported by Marquez et al. (Wysocki, R. J.; Siddiqui, M. A.; Barchi, J. J.; Driscoll, J. S.; Marquez, V. E. *Synthesis* 1991, 1005). D-ribose was converted in several steps to 1,3,5-tri-O-benzoyl-2-deoxy-2-fluoro-β-D-arabinofuranose, the corresponding bromo sugar derivative was produced under HBr/AcOH condition and the reaction of potassium carbonate in methanol gave the desired compound (Scheme E).

Scheme E

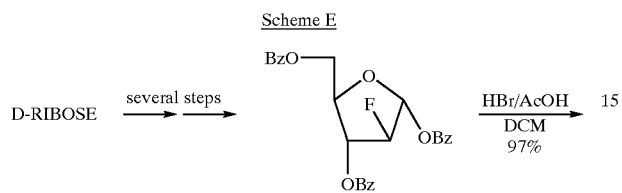
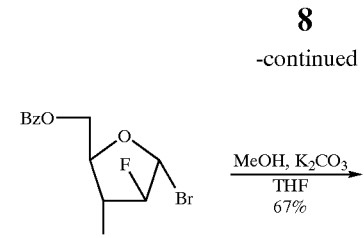

Reported Synthesis of 2-deoxy-2-fluoro-D-arabinopyranose 2-deoxy-2-fluoro-D-arabinopyranose was previously made from D-arabinose via D-arabinal as it is shown in Scheme F (Albano, E. L et al. *Carbohyd. Res.* 1971, 19, 63).

Scheme F

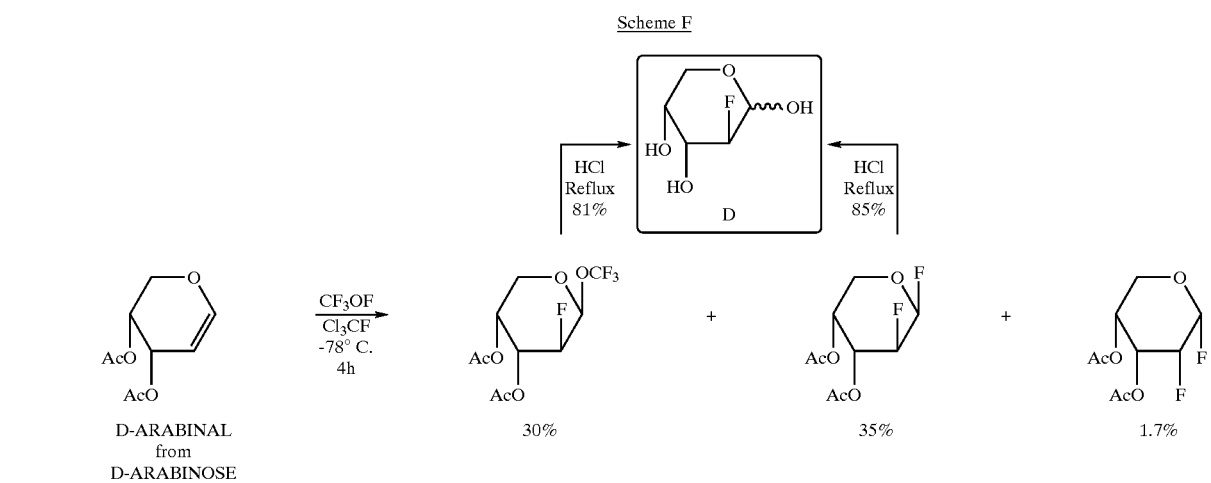

The same material was made from D-Ribose as shown below in Scheme G (Bols, M.; Lundt, I.; Acta Chem. Scand. 1990, 44, 252).

Scheme G

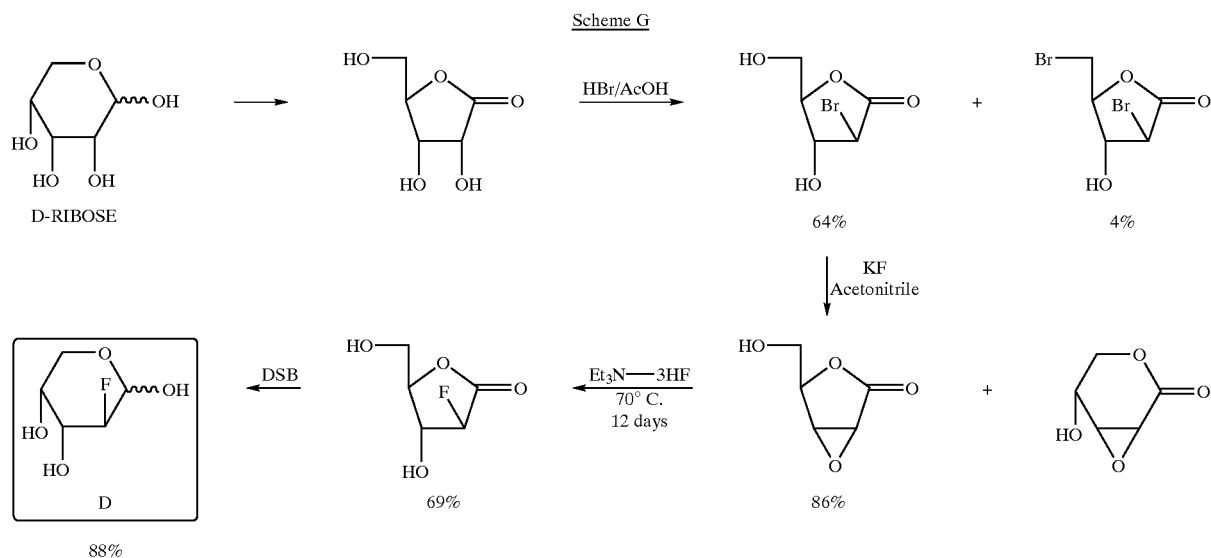

Reported Synthesis of 2-deoxy-2-fluoro-3,4-di-O-acetyl-D-arahinospyranose

The title compound was previously made as a result of an electrophilic addition of SELECTFLUOR™ on D-arabinal (Albert, M. et al, *Tetrahedron* 1998, 54, 4839; Scheme H).

Scheme H

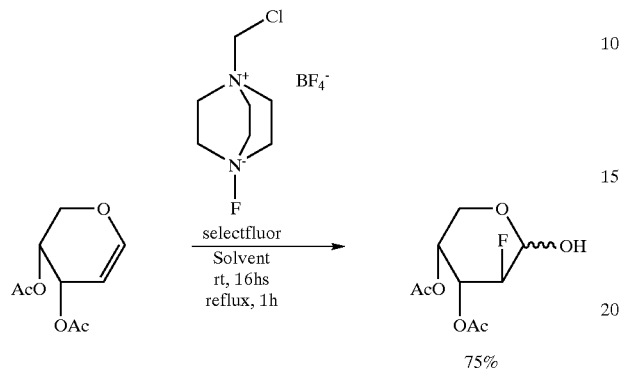

75%

In light of the commercial importance of L-FMAU, and its use in the treatment of patients afflicted with hepatitis B and Epstein Barr virus, it is an object of the invention to provide an improved synthesis of L-FMAU and related nucleosides.

It is another object of the invention to provide a synthesis of 2'-deoxy-2'-halo-β-L-arabinofuranosyl nucleosides from inexpensive starting materials in relatively high yield.

SUMMARY OF THE INVENTION

The present invention is a process for the preparation of 2'-deoxy-2'-halo-β-L-arabinofuranosyl nucleosides, and in particular, 2'-deoxy-2'-fluoro-β-L-arabinofuranosyl thymine (L-FMAU), from L-arabinose, which is commercially available and less expensive than L-ribose or L-xylose. The process involves the initial synthesis of a 2-deoxy-2-halo-3,4-di-O-protected-L-arabinospyranose, via an electrophilic halogenating agent, and in particular a fluorinating reagent. Deprotection and isomerization affords a 2-deoxy-2-halo-L-arabinofuranoside, a key intermediate in this synthesis. The 3- and 5-hydroxyl groups can then be protected, preferably by benzoylation, and the 1-position can be activated, preferably halogenated, and even more preferably brominated. This compound can then be condensed with a protected pyrimidine, purine, heterocyclic or heteroaromatic base to form the desired 2'-deoxy-2'-fluoro-L-arabinofuranosyl-nucleoside.

This process for the preparation of 2'-deoxy-2'-fluoro-L-arabinofuranosyl-nucleoside, and in particular, L-FMAU, is the first synthesis of this class of nucleosides from L-arabinose in ten steps. All of the reagents and starting materials are inexpensive and no special equipment is required to carry out the reactions. A key step for the synthesis is the conversion of a pyranoside, 2-deoxy-2-halo-L-arabinopyranose, into a furanoside, 2-deoxy-2-halo-L-arabinofuranoside.

In particular, in one embodiment of the present invention, a process for the preparation of a 2'-deoxy-2'-halo-β-L-arabinofuranosyl nucleoside of the formula (I):

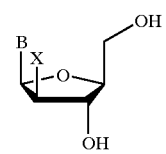

wherein X is a halogen (F, Cl, Br or I), though preferably fluorine; and B is a pyrimidine, purine, heterocyclic or heteroaromatic base; is provided, comprising (a) obtaining a 2-deoxy-2-halo-L-arabinopyranose of the formula (II):

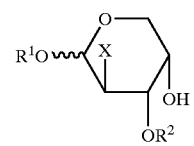

wherein each of $R^1$ and $R^2$ is independently hydrogen or a suitable oxygen protecting group such as alkyl, acyl or silyl;

(b) converting the 2-deoxy-2-halo-L-arabinopyranose to a 2-deoxy-2-halo-L-arabinofuranose;

(c) optionally substituting $OR^1$ with a suitable leaving group, such as O-Acyl (including OAc) or a halogen (F, Br, Cl or I), though preferably a halogen, and even more preferably Br;

(d) coupling the arabinofuranose to an optionally protected pyrimidine, purine, heterocyclic or heteroaromatic base; and (e) deprotecting, if necessary, to obtain the 2'-deoxy-2'-halo-β-L-arabinofuranosyl nucleoside.

In another embodiment of the invention, a process for the preparation of a 2'-deoxy-2'-halo-β-L-arabinofuranosyl nucleoside of the formula (I):

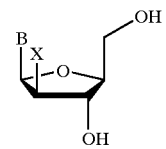

wherein X is a halogen (F, Cl, Br or I), though preferably fluorine; and B is a pyrimidine, purine, heterocyclic or heteroaromatic base; is provided, comprising (a) obtaining an optionally protected L-arabinose of the formula (IV):

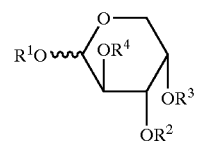

wherein each of $R^1$, $R^2$, $R^3$ and $R^4$ is independently hydrogen or a suitable oxygen protecting group such as alkyl, acyl or silyl;

(b) substituting $OR^1$ with a halogen (F, Br, Cl or I), preferably Br, to obtain a compound of the formula (V);

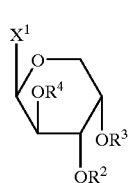

(V)

wherein X¹ is a halogen (F, Br, Cl or I), preferably Br;

(c) reducing the compound of formula (V) to form a compound of formula (III)

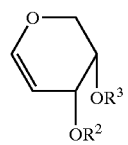

(III)

d) halogenating the compound of formula (III) and deprotecting if necessary to form the 2-deoxy-2-halo-L-arabinopyranose of the formula (II):

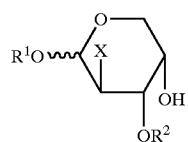

(II)

wherein X is a halogen (F, Br, Cl or I), preferably F;

(e) converting the 2-deoxy-2-halo-L-arabinopyranose to a 2-deoxy-2-halo-L-arabinofuranose;

(f) optionally substituting OR¹ with a suitable leaving group, such as O-Acyl (including OAc) or a halogen (F, Br, Cl or I), though preferably a halogen, and even more preferably Br;

(g) coupling the arabinofuranose to an optionally protected pyrimidine, purine, heterocyclic or heteroaromatic base; and (h) deprotecting, if necessary, to obtain the 2'-deoxy-2'-halo-β-L-arabinofuranosyl nucleoside.

In one particular embodiment of the present invention, the conversion of the 2-deoxy-2-halo-L-arabinopyranose to a 2-deoxy-2-halo-L-arabinofuranose is accomplished using one equivalent of sulfuric acid. In a further embodiment of the present invention, the conversion of the 2-deoxy-2-halo-L-arabinopyranose to a 2-deoxy-2-halo-L-arabinofuranose is accomplished in dry methanol. In a preferred embodiment, the conversion of the 2-deoxy-2-halo-L-arabinopyranose to a 2-deoxy-2-halo-L-arabinofuranose is accomplished using one equivalent of sulfuric acid in dry methanol.

In another embodiment of the present invention, a process for the preparation of 2'-deoxy-2'-fluoro-β-L-arabinofuranosyl thymine (L-FMAU) comprising (a) obtaining a 2-deoxy-2-fluoro-L-arabinopyranose of the formula (II-a):

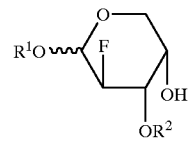

(II-a)

wherein each of R¹ and R² is independently hydrogen or a suitable oxygen protecting group such as alkyl, acyl or silyl;

(b) converting the 2-deoxy-2-fluoro-L-arabinopyranose to a 2-deoxy-2-fluoro-L-arabinofuranose;

(c) optionally substituting OR¹ with a suitable leaving group, such as O-Acyl (including OAc) or a halogen (F, Br, Cl or I), though preferably a halogen, and even more preferably Br;

(d) coupling the arabinofuranose to an optionally protected thymidine; and (e) deprotecting, if necessary, to obtain the 2'-deoxy-2'-fluoro-β-L-arabinofuranosyl thymidine.

In yet another embodiment of the invention, a process for the preparation of 2'-deoxy-2'-fluoro-β-L-arabinofuranosyl thymine (L-FMAU) comprising (a) obtaining an optionally protected L-arabinose of the formula (IV):

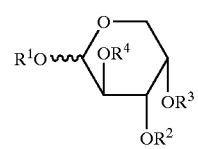

(IV)

wherein each of R¹, R², R³ and R⁴ is independently hydrogen or a suitable oxygen protecting group such as alkyl, acyl or silyl;

(b) substituting OR¹ with a halogen (F, Br, Cl or I), preferably Br, to obtain a compound of the formula (V);

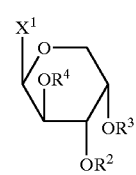

(V)

wherein X¹ is a halogen (F, Br, Cl or I), preferably Br;

(c) reducing the compound of formula (V) to form a compound of formula (III)

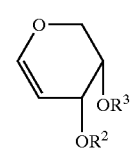

(III)

(d) fluorinating the compound of formula (III) and deprotecting if necessary to form the 2-deoxy-2-fluoro-L-arabinopyranose of the formula (II-a);

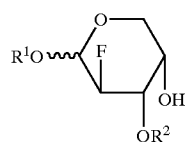

(f) converting the 2-deoxy-2-fluoro-L-arabinopyranose to a 2-deoxy-2-fluoro-L-arabinofuranose;

(g) optionally substituting OR¹ with a suitable leaving group, such as O-Acyl (including OAc) or a halogen (F, Br, Cl or I), though preferably a halogen, and even more preferably Br;

(h) coupling the arabinofuranose to an optionally protected thymine; and (i) deprotecting, if necessary, to obtain the 2'-deoxy-2'-fluoro-β-L-arabinofuranosyl thymidine.

In a particular embodiment of the present invention, the halogenation, and in particular, the fluorination, of the compound of formula (III) is accomplished in nitromethane: water. In an alternate embodiment, the halogenation, and in particular, the fluorination, of the compound of formula (III) is accomplished in acetone: water.

In one particular embodiment of the present invention, the conversion of the 2-deoxy-2-fluoro-L-arabinopyranose to a 2-deoxy-2-fluoro-L-arabinofuranose is accomplished using one equivalent of sulfuric acid. In a further embodiment of the present invention, the conversion of the 2-deoxy-2-fluoro-L-arabinopyranose to a 2-deoxy-2-fluoro-L-arabinofuranose is accomplished in dry methanol. In a preferred embodiment, the conversion of the 2-deoxy-2-fluoro-L-arabinopyranose to a 2-deoxy-2-fluoro-L-arabinofuranose is accomplished using one equivalent of sulfuric acid in dry methanol.

In one embodiment of the invention the 2'-deoxy-2'-halo-β-L-arabinofuranosyl nucleoside, and in particular the 2'-deoxy-2'-fluoro-β-L-arabinofuranosyl thymine, can be further functionalized, such as phosphorylated or acylated to form pharmaceutically acceptable salts or prodrugs.

DETAILED DESCRIPTION OF THE INVENTION

Figure 1:
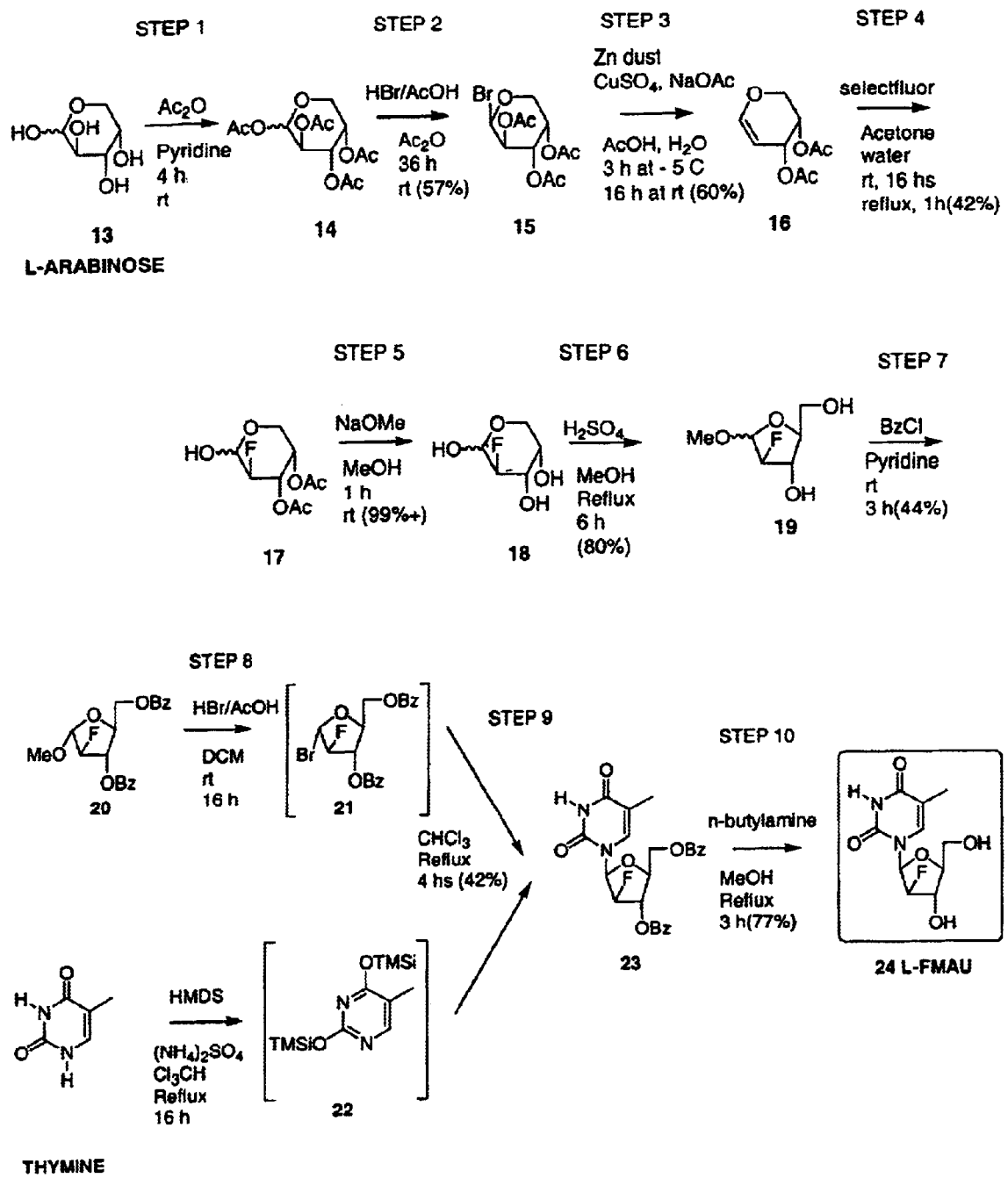
FIG. 1 is a non-limiting example of a process for the preparation of 2'-deoxy-2'-fluoro-β-L-arabinofuranosyl thymine, according to the present invention.

The present invention is a process for the preparation of 2'-deoxy-2'-halo-β-L-arabinofuranosyl nucleosides, and in particular, 2'-deoxy-2'-fluoro-β-L-arabinofuranosyl thymine (L-FMAU), from L-arabinose, which is commercially available and less expensive than L-ribose or L-xylose. The process involves the initial synthesis of a 2-deoxy-2-halo-3,4-di-O-protected-L-arabinospyranose, and in particular 2-deoxy-2-fluoro-3,4-di-O-acetyl-L-arabinospyranose, via an electrophilic halogenating agent, and in particular a fluorinating reagent. Deprotection and isomerization affords a 2-deoxy-2-halo-L-arabinofuranoside, and in particular, 1-O-methyl-2-deoxy-2-fluoro-L-arabinofuranoside, a key intermediate in this synthesis. The 3- and 5-hydroxyl groups can then be protected, preferably by benzoylation, and the 1-position can be activated, preferably halogenated, and even more preferably brominated to form, for example, 1-bromo-3,5-di-O-benzoyl-2-deoxy-2-fluoro-L-arbinofuranose. This compound can then be condensed with a protected pyrimidine, purine, heterocyclic or heteroaromatic base to form the desired 2'-deoxy-2'-fluoro-L-arabinofuranosyl-nucleoside.

This process for the preparation of 2'-deoxy-2'-fluoro-L-arabinofuranosyl-nucleoside, and in particular, L-FMAU, is the first synthesis of this class of nucleosides from L-arabinose in ten steps. All of the reagents and starting materials are inexpensive and no special equipment is required to carry out the reactions. A key step for the synthesis is the conversion of a pyranoside, 2-deoxy-2-halo-L-arabinopyranose, into a furanoside, 2-deoxy-2-halo-L-arabinofuranoside.

The term "L-FMAU analog" or "related nucleoside" as used herein refers to a nucleoside that is formed from a pyrimidine or purine base that is coupled to a 2-fluoro-arabinofuranosyl moiety.

In particular, in one embodiment of the present invention, a process for the preparation of a 2'-deoxy-2'-halo-β-L-arabinofuranosyl nucleoside of the formula (I):

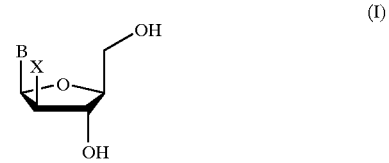

wherein X is a halogen (F, Cl, Br or I), though preferably fluorine; and B is a pyrimidine, purine, heterocyclic or heteroaromatic base; is provided, comprising (a) obtaining a 2-deoxy-2-halo-L-arabinopyranose of the formula (II):

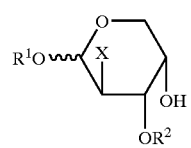

wherein each of R¹ and R² is independently hydrogen or a suitable oxygen protecting group such as alkyl, acyl or silyl;

(b) converting the 2-deoxy-2-halo-L-arabinopyranose to a 2-deoxy-2-halo-L-arabinofuranose;

(c) optionally substituting OR¹ with a suitable leaving group, such as O-Acyl (including OAc) or a halogen (F, Br, Cl or I), though preferably a halogen, and even more preferably Br;

(d) coupling the arabinofuranose to an optionally protected pyrimidine, purine, heterocyclic or heteroaromatic base; and (e) deprotecting, if necessary, to obtain the 2'-deoxy-2'-halo-β-L-arabinofuranosyl nucleoside.

In a particular embodiment of the invention, the 2-deoxy-2-halo-L-arabinopyranose of the formula (II):

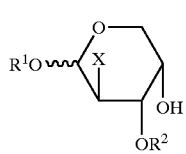

(II)

wherein R¹ and R² is as defined above, is provided by a process, comprising
(a) obtaining an optionally protected L-arabinal of the formula (III)

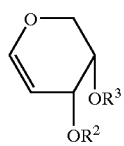

(III)

wherein each of R³ is independently hydrogen or a suitable oxygen protecting group such as alkyl, acyl or silyl;
(b) halogenating the compound of formula (III) and deprotecting, if necessary, to form the 2-deoxy-2-halo-L-arabinopyranose of the formula (II).

In an even more particular embodiment of the invention, the 2-deoxy-2-halo-L-arabinopyranose of the formula (II):

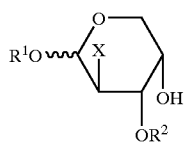

(II)

wherein R¹ and R² is as defined above, is provided by a process, comprising
(a) obtaining an optionally protected L-arabinose of the formula (IV):

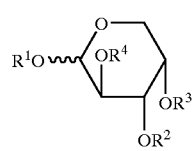

(IV)

wherein each of R³ and R⁴ is independently hydrogen or a suitable oxygen protecting group such as alkyl, acyl or silyl;
(b) substituting OR¹ with a halogen (F, Br, Cl or I), preferably Br, to obtain a compound of the formula (V);

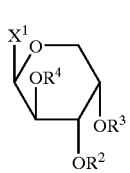

(V)

wherein X¹ is a halogen (F, Br, Cl or I), preferably Br;
(c) reducing the compound of formula (V) to form a compound of formula (III)

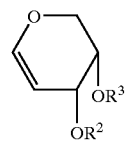

(III)

(d) halogenating the compound of formula (III) and deprotecting if necessary to form the 2-deoxy-2halo-L-arabinopyranose of the formula (II).

In one embodiment of the invention, a process for the preparation of a 2'-deoxy-2'-halo-β-L-arabinofuranosyl nucleoside of the formula (I):

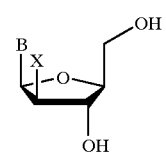

(I)

wherein X is a halogen (F, Cl, Br or I), though preferably fluorine; and B is a pyrimidine, purine, heterocyclic or heteroaromatic base; is provided, comprising
(a) obtaining an optionally protected L-arabinose of the formula (IV):

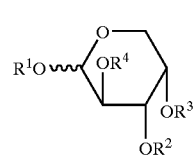

(IV)

wherein each of R¹, R², R³ and R⁴ is independently hydrogen or a suitable oxygen protecting group such as alkyl, acyl or silyl;
(b) substituting OR¹ with a halogen (F, Br, Cl or I), preferably Br, to obtain a compound of the formula (V);

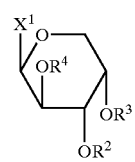

(V)

wherein X¹ is a halogen (F, Br, Cl or I), preferably Br;
(c) reducing the compound of formula (V) to form a compound of formula (III)

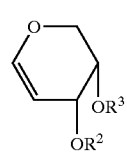

(III)

(d) halogenating the compound of formula (III) and deprotecting if necessary to form the 2-deoxy-2-halo-L-arabinopyranose of the formula (II):

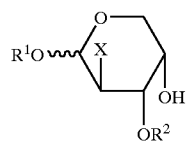

(II)

wherein X is a halogen (F, Br, Cl or I), preferably F;

(e) converting the 2-deoxy-2-halo-L-arabinopyranose to a 2-deoxy-2-halo-L-arabinofuranose;

(f) optionally substituting $OR^1$ with a suitable leaving group, such as O-Acyl (including OAc) or a halogen (F, Br, Cl or I), though preferably a halogen, and even more preferably Br;

(g) coupling the arabinofuranose to an optionally protected pyrimidine, purine, heterocyclic or heteroaromatic base; and (h) deprotecting, if necessary, to obtain the 2'-deoxy-2'-halo-β-L-arabinofuranosyl nucleoside.

In one particular embodiment of the present invention, the conversion of the 2-deoxy-2-halo-L-arabinopyranose to a 2-deoxy-2-halo-L-arabinofuranose is accomplished using one equivalent of sulfuric acid. In a further embodiment of the present invention, the conversion of the 2-deoxy-2-halo-L-arabinopyranose to a 2-deoxy-2-halo-L-arabino-furanose is accomplished in dry methanol. In a preferred embodiment, the conversion of the 2-deoxy-2-halo-L-arabinopyranose to a 2-deoxy-2-halo-L-arabinofuranose is accomplished using one equivalent of sulfuric acid in dry methanol.

In another embodiment of the present invention, a process for the preparation of 2'-deoxy-2'-fluoro-β-L-arabinofuranosyl thymine (L-FMAU) comprising (a) obtaining a 2-deoxy-2-fluoro-L-arabinopyranose of the formula (II-a):

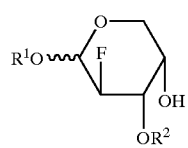

(II-a)

wherein each of $R^1$ and $R^2$ is independently hydrogen or a suitable oxygen protecting group such as alkyl, acyl or silyl;

(b) converting the 2-deoxy-2-fluoro-L-arabinopyranose to a 2-deoxy-2-fluoro-L-arabinofuranose;

(c) optionally substituting $OR^1$ with a suitable leaving group, such as O-Acyl (including OAc) or a halogen (F, Br, Cl or I), though preferably a halogen, and even more preferably Br;

(d) coupling the arabinofuranose to an optionally protected thymidine; and (e) deprotecting, if necessary, to obtain the 2'-deoxy-2'-fluoro-β-L-arabinofuranosyl thymidine.

In a particular embodiment of the invention, the 2-deoxy-2-fluoro-L-arabinopyranose of the formula (II-a):

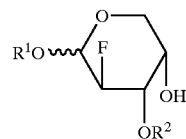

(II-a)

wherein $R^1$ and $R^2$ is as defined above, is provided by a process, comprising (a) obtaining an optionally protected L-arabinal of the formula (III)

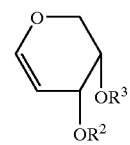

(III)

wherein each of $R^3$ is independently hydrogen or a suitable oxygen protecting group such as alkyl, acyl or silyl;

(b) fluorinating the compound of formula (III) and deprotecting, if necessary, to form the 2-deoxy-2-fluoro-L-arabinopyranose of the formula (II-a).

In an even more particular embodiment of the invention, the 2-deoxy-2-halo-L-arabinopyranose of the formula (II-a):

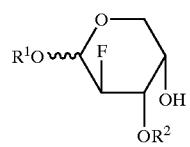

(II-a)

wherein $R^1$ and $R^2$ is as defined above, is provided by a process, comprising (a) obtaining an optionally protected L-arabinose of the formula (IV):

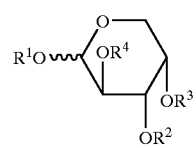

(IV)

wherein each of $R^3$ and $R^4$ is independently hydrogen or a suitable oxygen protecting group such as alkyl, acyl or silyl;

(b) substituting $OR^1$ with a halogen (F, Br, Cl or I), preferably Br, to obtain a compound of the formula (V);

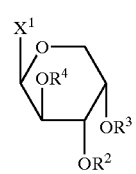

(V)

wherein $X^1$ is a halogen (F, Br, Cl or I), preferably Br;

(c) reducing the compound of formula (V) to form a compound of formula (III)

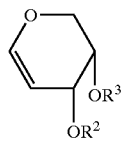
(III)

(d) fluorinating the compound of formula (III) and deprotecting if necessary to form the 2-deoxy-2-fluoro-L-arabinopyranose of the formula (II-a).

In one embodiment of the invention, a process for the preparation of 2'-deoxy-2'-fluoro-β-L-arabinofuranosyl thymine (L-FMAU) comprising (a) obtaining an optionally protected L-arabinose of the formula (IV):

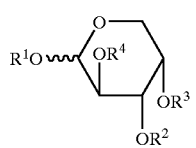
(IV)

wherein each of $R^1$, $R^2$, $R^3$ and $R^4$ is independently hydrogen or a suitable oxygen protecting group such as alkyl, acyl or silyl;

(b) substituting $OR^1$ with a halogen (F, Br, Cl or I), preferably Br, to obtain a compound of the formula (V);

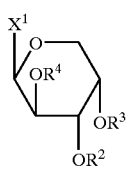
(V)

wherein $X^1$ is a halogen (F, Br, Cl or I), preferably Br;

(c) reducing the compound of formula (V) to form a compound of formula (III)

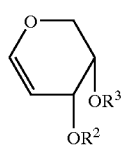
(III)

(d) fluorinating the compound of formula (III) and deprotecting if necessary to form the 2-deoxy-2-fluoro-L-arabinopyranose of the formula (II-a);

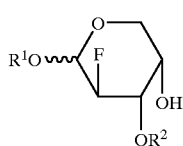
(II-a)

(f) converting the 2-deoxy-2-fluoro-L-arabinopyranose to a 2-deoxy-2-fluoro-L-arabinofuranose;

(g) optionally substituting $OR^1$ with a suitable leaving group, such as O-Acyl (including OAc) or a halogen (F, Br, Cl or I), though preferably a halogen, and even more preferably Br;

(h) coupling the arabinofuranose to an optionally protected thymine; and (i) deprotecting, if necessary, to obtain the 2'-deoxy-2'-fluoro-β-L-arabinofuranosyl thymidine.

In a particular embodiment of the present invention, the halogenation, and in particular, the fluorination, of the compound of formula (III) is accomplished in nitromethane: water. In an alternate embodiment, the halogenation, and in particular, the fluorination, of the compound of formula (III) is accomplished in acetone: water.

In one particular embodiment of the present invention, the conversion of the 2-deoxy-2-fluoro-L-arabinopyranose to a 2-deoxy-2-fluoro-L-arabinofuranose is accomplished using one equivalent of sulfuric acid. In a further embodiment of the present invention, the conversion of the 2-deoxy-2-fluoro-L-arabinopyranose to a 2-deoxy-2-fluoro-L-arabinofuranose is accomplished in dry methanol. In a preferred embodiment, the conversion of the 2-deoxy-2-fluoro-L-arabinopyranose to a 2-deoxy-2-fluoro-L-arabinofuranose is accomplished using one equivalent of sulfuric acid in dry methanol.

Non limiting examples of fluorinating agents that can be used in the electrophilic addition of fluorine to L-arabinal include: trifluoromethyl hypofluorite ($CF_3OF$), acetyl hypoflurite ($CH_3COOF$), xenon difluoride ($XeF_2$), elemental fluorine ($F_2$). In a preferred embodiment the fluorinating agent is SELECTFLUOR™ (F-TEDA-$BF_4$).

I. Nucleosides which can be Synthesized According to the Present Invention

The invention as disclosed herein can be used to produce compounds of formula (C).

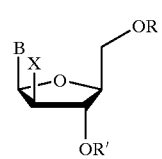
(C)

wherein each R and R' is independently hydrogen, alkyl, acyl, aryl, monophosphate, diphosphate, triphosphate, amino acid, or an oxygen protecting group;

X is a halogen (F, Cl, Br or I), and preferably fluorine; and

B is a pyrimidine, purine, heterocyclic or heteroaromatic base.

These compounds either possess antiviral (i.e., anti-hepatitis B virus or anti-Epstein-Barr virus) activity, are metabolized to a compound that exhibits such activity, or can be used in a manufacturing process to prepare compounds having such activity.

II. Definitions

As used herein, the term "substantially free of" or "substantially in the absence of" refers to a nucleoside composition that includes at least 95% to 98%, or more preferably, 99% to 100%, of the designated enantiomer of that nucleoside. In a preferred embodiment, the compound is prepared substantially free of its corresponding β-D isomer.

The term "enantiomerically enriched" is used throughout the specification to describe a nucleoside which includes at least about 95%, preferably at least 96%, more preferably at least 97%, even more preferably, at least 98%, and even more preferably at least about 99% or more of a single enantiomer of that nucleoside. When a nucleoside of a particular configuration (D or L) is referred to in this specification, it is presumed that the nucleoside is an enantiomerically enriched nucleoside, unless otherwise stated.

The term alkyl, as used herein, unless otherwise specified, refers to a saturated straight, branched, or cyclic, primary, secondary, or tertiary hydrocarbon, typically of $C_1$ to $C_{18}$, includes lower alkyl, and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl and 2,3-dimethyl-butyl. The alkyl group can be optionally substituted with functional groups as desired, as known to those skilled in the art, for example, as taught in Greene, et al., *Protective Groups in Organic Synthesis*, John Wiley and Sons, Second Edition, 1991, hereby incorporated by reference. The term lower alkyl, as used herein, and unless otherwise specified, refers to a $C_1$ to $C_4$ saturated straight, branched, or if appropriate, a cyclic (for example, cyclopropyl) alkyl group, including both substituted and unsubstituted forms.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art or organic synthesis. Suitable protecting groups are described, for example, in Greene, et al. "Protective Groups in Organic Synthesis," John Wiley and Sons, Second Edition, 1991, hereby incorporated by reference.

The term aryl, as used herein, and unless otherwise specified, refers to phenyl, biphenyl, or naphthyl, and preferably phenyl. The aryl group can be optionally substituted as known to those skilled in the art, for example, as taught in Greene, et al., "Protective Groups in Organic Synthesis," John Wiley and Sons, Second Edition, 1991.

The term acyl refers to moiety of the formula —C(O)R', wherein R' is alkyl; aryl, alkaryl, aralkyl, heteroaromatic, heterocyclic, alkoxyalkyl including methoxymethyl; arylalkyl including benzyl; aryloxyalkyl, such as phenoxymethyl; aryl including phenyl optionally substituted with halo groups $C_1$ to $C_4$ alkyl or $C_1$ to $C_4$ alkoxy or the residue of an amino acid.

The term silyl refers to moiety of the formula —SiR'$_3$, wherein each R' is independently alkyl or aryl group as defined herein. The alkyl or aryl group can be optionally substituted as known to those skilled in the art, for example, as taught in Greene, et al., "Protective Groups in Organic Synthesis," John Wiley and Sons, Second Edition, 1991.

The term "halogen," as used herein, includes fluorine, chlorine, bromine and iodine.

The term purine or pyrimidine base includes, but is not limited to, adenine, 6-alkylpurines, 6-acylpurines (wherein acyl is C(O)(alkyl, aryl, alkylaryl, or arylalkyl), 6-benzylpurine, 6-halopurine, $N^6$-acyl purine, 6-hydroxyalkyl purine, 6-thioalkyl purine, $N^2$-alkylpurines, $N^2$-alkyl-6-thiopurines, thymine, cytosine, 5-fluorocytosine, 5-methyl-cytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzyl-pyrimidines, $C^5$-halopyrimidines, $C^5$-vinylpyrimidine, $C^5$-acetylenic pyrimidine, $C^5$-acyl pyrimidine, $C^5$-hydroxyalkyl pyrimidine, $C^5$-amidopyrimidine, $C^5$-cyanopyrimidine, $C^5$-nitropyrimidine, $C^5$-aminopyrimidine, 5-azacytidinyl, 5-azauracilyl, triazolopyridinyl, imidazolopyridinyl, pyrrolopyrimidinyl and pyrazolopyrimidinyl. Purine bases include, but are not limited to, guanine, adenine, hypoxanthine, 2,6-diaminopurine, and 6-chloro-purine. Functional oxygen and nitrogen groups on the base can be protected as necessary or desired. Suitable protecting groups are well known to those skilled in the art, and include trimethylsilyl, dimethylhexylsilyl, t-butyldimethylsilyl and t-butyldiphenylsilyl, trityl, alkyl groups, acyl groups such as acetyl and propionyl, methanesulfonyl, and p-toluenesulfonyl. The heteroaromatic group can be optionally substituted as described above for aryl.

The term heteroaryl or heteroaromatic, as used herein, refers to an aromatic that includes at least one sulfur, oxygen, nitrogen or phosphorus in the aromatic ring. The term heterocyclic refers to a nonaromatic cyclic group wherein there is at least one heteroatom, such as oxygen, sulfur, nitrogen or phosphorus in the ring. Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinypurine, $N^6$-acetylenic purine, $N^6$-acyl purine,$N^6$-hydroxyalkyl purine, $N^6$-thioalkyl purine, thymine, cytosine, 6-azapyrimidine, 2-mercaptopyrmidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic group can be optionally substituted as described above for aryl. The heterocyclic or heteroaromatic group can be optionally substituted with one or more substituent selected from halogen, haloalkyl, alkyl, alkoxy, hydroxy, carboxyl derivatives, amido, amino, alkylamino, dialkylamino. The heteroaromatic can be partially or totally hydrogenated as desired. As a nonlimiting example, dihydropyridine can be used in place of pyridine. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyl-diphenylsilyl, trityl or substituted trityl, alkyl groups, acyl groups such as acetyl and propionyl, methanesulfonyl, and p-toluenylsulfonyl.

These purine or pyrimidine bases, heteroaromatics and heterocycles can be substituted with alkyl groups or aromatic rings, bonded through single or double bonds or fused to the heterocycle ring system. The purine base, pyrimidine base, heteroaromatic or heterocycle may be bound to the sugar moiety through any available atom, including the ring nitrogen and ring carbon (producing a C-nucleoside).

III. Detailed Description of the Process Steps
Preparation of Starting Material—2-deoxy-2-halo-L-arabinopyranose (II)

The key starting material for this process is an appropriately substituted 2-deoxy-2-halo-L-arabinopyranose (II). The 2-deoxy-2-halo-L-arabinopyranose (II) can be purchased or can be prepared by any known means including standard reduction and electrophilic addition techniques. In one embodiment, the 2-deoxy-2-halo-L-arabinopyranose (II) is prepared from L-arabinal followed by halogenation. The L-arabinal can be purchased or can be prepared by any known means including standard reduction techniques. For example, the L-arabinal can be prepared from an appropriately protected L-arabinose, preferably protected with an acyl group such as with an acetyl group, according to the following protocol.

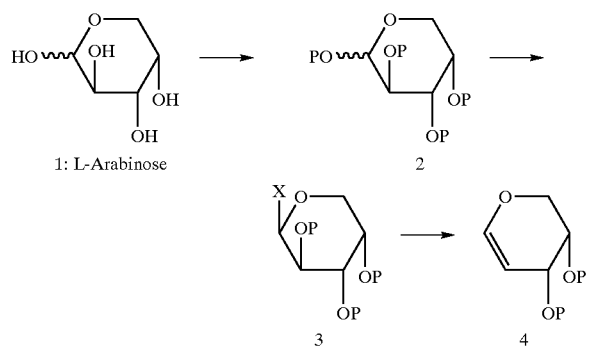

L-Arabinose (1) can be protected by methods well known to those skilled in the art, as taught in Greene, et al., *Protective Groups in Organic Synthesis*, John Wiley and Sons, Second Edition, 1991, to form an appropriately protected L-arabinose (2), wherein each P is independently hydrogen or an appropriate oxygen protecting group such as an alkyl, acyl or silyl group, though preferably an acyl group such as an acetyl group. The protection can be carried out in any appropriate solvent that facilitates the desired result. In one embodiment the reaction is carried out in a mild base, such as pyridine. This reaction can be accomplished at any temperature that allows the reaction to proceed at an acceptable rate without promoting decomposition or excessive side products. The preferred temperature is from 0° C. to room temperature.

The appropriately substituted L-arabinose (2) can then be halogenated, preferably brominated, using an appropriate halide under any suitable conditions, though preferably acidic conditions, to obtain a 1-α-halo-2,3,4-tri-O-protected-L-arabinopyranose (3), such as 1-α-bromo-2,3,4-tri-O-acetyl-L-arabinopyranose. The halogenation can be carried out in any appropriate solvent that facilitates the desired result. In one non-limiting example, compound (2) can be halogenated with H—X, wherein X is F, Cl, Br or I, though preferably Br, optionally with a suitable acid, preferably an acyl acid such as acetic acid, optionally with an acyl anhydride such as acetic anhydride. This reaction can be accomplished at any temperature that allows the reaction to proceed at an acceptable rate without promoting decomposition or excessive side products. The preferred temperature is from room temperature to refluxing conditions.

The 1-α-halo-2,3,4-tri-O-protected-L-arabinopyranose (3) can then be reduced using any suitable reducing agent to obtain the L-arabinal (4). Possible reducing agents are reagents that promote reduction, including but not limited to, zinc dust in the presence of $CuSO_4$·pentahydrate and sodium acetate in $AcOH/H_2O$. This reaction can be accomplished at any temperature that allows the reaction to proceed at an acceptable rate without promoting decomposition or excessive side products. The preferred temperature is from below −5° C. to room temperature. The L-arabinal can be prepared in any solvent that is suitable for the temperature and the solubility of the reagents. Solvents can consist of any protic solvent including, but not limiting to, alcohol, such as methanol, ethanol, isopropanol, butanol, pentanol or hexanol, acyl acid such as acetic acid, water or any combination thereof, though preferably the solvent is acetic acid and water.

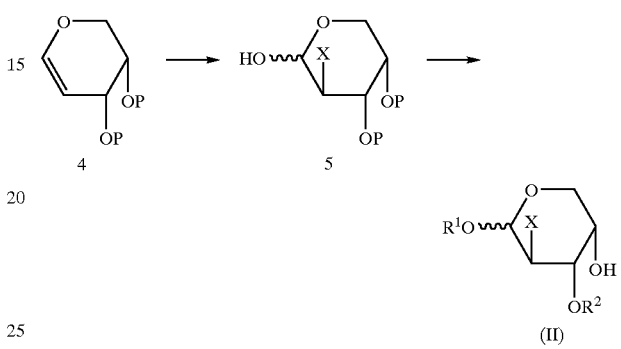

The L-arabinal (4) can then be halogenated, preferably fluorinated, using an appropriate electrophilic halogenating reagent to afford compound (5). Possible electrophilic halogenating agents are reagents that promote regiospecific halogenation. In one particular embodiment, an electrophilic fluorinating agent is used. Non-limiting examples of fluorinating agents that can be used in the electrophilic addition of fluorine to L-arabinal include, but not limited to, trifluoromethyl hypofluorite ($CF_3OF$), acetyl hypoflurite ($CH_3COOF$), xenon difluoride ($XeF_2$), elemental fluorine ($F_2$). In an alternate embodiment the fluorinating agent is SELECTFLUOR™. This reaction can be accomplished at any temperature that allows the reaction to proceed at an acceptable rate without promoting decomposition or excessive side products. The preferred temperature is from room temperature to refluxing conditions. The halogenation can be prepared in any solvent that is suitable for the temperature and the solubility of the reagents. Solvents can consist of any polar protic or aprotic solvent including, but not limiting to, alcohol, such as methanol, ethanol, isopropanol, butanol, pentanol or hexanol, acetone, ethyl acetate, dithianes, THF, dioxane, acetonitrile, nitromethane, dimethylformamide (DMF), dimethylsulfoxide (DMSO), dimethyl-acetamide, water, or any combination thereof, though preferably the solvent is water/nitromethane and water/acetone: (1/2).

The optionally protected 2-deoxy-2-halo-L-arabinopyranose (5) can then be deprotected, if necessary, by methods well known to those skilled in the art, as taught in Greene, et al., *Protective Groups in Organic Synthesis*, John Wiley and Sons, Second Edition, 1991, to obtain the 2-deoxy-2-halo-L-arabinopyranose (II). The deprotection can be carried out in any appropriate solvent that facilitates the desired result. This reaction can be accomplished at any temperature that allows the reaction to proceed at an acceptable rate without promoting decomposition or excessive side products. For example, acyl protecting groups, and in particular an acetyl group, can be deprotected with sodium methoxide in methanol at room temperature.

In one preferred embodiment of the invention, this procedure, can be tailored to produce the critical intermediate compounds for the synthesis of L-FMAU or L-FMAU analogs.

Preparation of 2-deoxy-2-halo-L-arabinofuranose

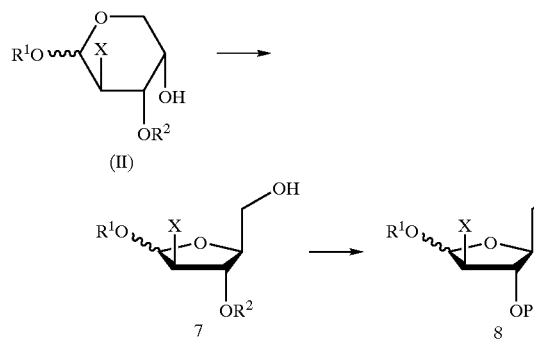

The 2-deoxy-2-halo-L-arabinopyranose (II) is reacted with any suitable acid (in gas or liquid form), such as, but not limited to sulfuric or hydrochloric acid in either catalytic amounts or in excess to form a 2-deoxy-2-halo-L-arabinofuranose (7). In a one embodiment of the present invention, 1 molar equivalent of sulfuric acid is used for this reaction. This reaction can be accomplished at any temperature that allows the reaction to proceed at an acceptable rate without promoting decomposition or excessive side products. The preferred temperature is from room temperature to refluxing conditions. This reaction can be carried out in any solvent that is suitable for the temperature and the solubility of the reagents. Solvents can consist of any polar protic or aprotic solvent including, but not limiting to, an alcohol, such as methanol, ethanol, isopropanol, butanol, pentanol or hexanol, acetone, ethyl acetate, dithianes, THF, dioxane, acetonitrile, nitromethane, dimethylformamide (DMF), dimethylsulfoxide (DMSO), dimethyl-acetamide, water, or any combination thereof, though preferably the solvent is methanol.

The 2-deoxy-2-halo-L-arabinofuranose (7) can be optionally protected by methods well known to those skilled in the art, as taught in Greene, et al., *Protective Groups in Organic Synthesis*, John Wiley and Sons, Second Edition, 1991, to form an appropriately protected 2-deoxy-2-halo-L-arabinofuranose (8), wherein each P is independently hydrogen or an appropriate oxygen protecting group such as an alkyl, acyl or silyl group, though preferably an acyl group such as a benzoyl group. The protection can be carried out in any appropriate solvent that facilitates the desired result. In one embodiment the reaction is carried out in a mild base, such as pyridine. This reaction can be accomplished at any temperature that allows the reaction to proceed at an acceptable rate without promoting decomposition or excessive side products. The preferred temperature is from 0° C. to room temperature.

Preparation of 2'-deoxy-2'-halo-β-L-arabinofuranosyl nucleoside

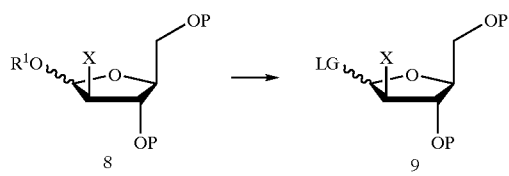

The appropriately protected 2-deoxy-2-halo-L-arabinofuranose (8) is optionally activated to form an activated 2-deoxy-2-halo-L-arabinofuranose (9), wherein LG is a suitable leaving group, such as O-Acyl (including OAc) or a halogen (F, Br, Cl or I), though preferably a halogen, and even more preferably Br. In one non-limiting example, compound (8) is halogenated with halogenated with H—X, wherein X is F, Cl, Br or I, though preferably Br, optionally with a suitable acid, preferably an acyl acid such as acetic acid, to afford compound (9). This reaction can be accomplished at any temperature that allows the reaction to proceed at an acceptable rate without promoting decomposition or excessive side products. The preferred temperature is room temperature. This reaction can be carried out in any solvent that is suitable for the temperature and the solubility of the reagents. Solvents can consist of any polar protic or aprotic solvent including, but not limiting to, an alcohol, such as methanol, ethanol, isopropanol, butanol, pentanol or hexanol, acetone, ethyl acetate, dithianes, THF, dioxane, acetonitrile, nitromethane, dichloromethane, dichloroethane, diethyl ether, dimethylformamide (DMF), dimethylsulfoxide (DMSO), dimethyl-acetamide, water, or any combination thereof, though preferably the solvent is dichloromethane.

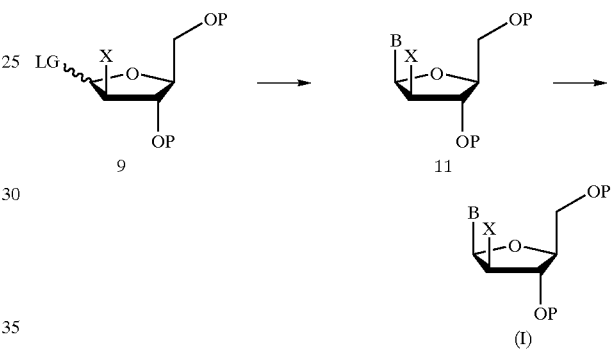

The activated 2-deoxy-2-halo-L-arabinofuranose (9) can then be coupled with an optionally protected pyrimidine, purine, heterocyclic or heteroaromatic base to afford the optionally protected 2'-deoxy-2'-halo-L-arabinonucleoside (11). Solubilizing substituents can be added to the purine base, pyrimidine base, heteroaromatic or heterocycle to promote solubility in the desired solvent system. It should also be understood that certain functional groups of the purine base, pyrimidine base, heteroaromatic or heterocycle might need to be protected to prevent unnecessary side reactions. The reactive moieties can be protected using conventional means and appropriate protecting groups well known to those skilled in the art, as taught in Greene, et al., *Protective Groups in Organic Synthesis*, John Wiley and Sons, Second Edition, 1991. For example, the free amine on cytosine may be protected by reaction with benzoyl chloride or any other suitable acyl compound to prevent unnecessary coupling at the $N^4$ position, to activate the cytosine base, and/or to assist in solubilizing the compound in the organic solvent. Alternatively, the free amine and/or free hydroxyl on the purine base, pyrimidine base, heteroaromatic or heterocycle, such as thymine, may be protected with a silyl group, such as trimethylsilyl chloride to prevent unnecessary side products, to activate the purine base, pyrimidine base, heteroaromatic or heterocycle, such as thymine, and/or to assist in solubilizing the compound in the organic solvent. Any compound containing a nitrogen that is capable of reaction with a center of electron deficiency can be used in the condensation reaction. In one embodiment an O-protected thymine base, for example a silylated thymine such as trimethylsilyl-thymine, is coupled with compound (9). In a preferred embodiment, the pyrimidine or purine base is silylated with a suitable silylating agent to form a silylated base. Possible silylating agents are reagents that promote silylation, including but not limited to, 1,1,1,3,3,3-hexamthyldisilazane, optionally with a catalytic amount of ammonium sulfate. This reaction can be accomplished at any temperature that allows the reaction to proceed at an acceptable rate without promoting decomposition or excessive side products. The preferred temperature is refluxing conditions.

The coupling reaction can be accomplished at any temperature that allows the reaction to proceed at an acceptable rate without promoting decomposition or excessive side products. The preferred temperature is room temperature. The reaction can take place in any solvent that provides the appropriate temperature and the solubility of the reagents. Examples of solvents include any aprotic solvent such as an alkyl solvent such as hexane and cyclohexane, toluene, acetone, ethyl acetate, dithianes, THF, dioxane, acetonitrile, chloroform, dichloromethane, dichloroethane, diethyl ether, pyridine, dimethylformamide (DMF), dimethylsulfoxide (DMSO), dimethylacetamide, 1,1,1,3,3,3-hexamehtyldisilazane or any combination thereof, preferably dichloromethane, dichloro-ethane or a combination of chloroform and 1,1,1,3,3,3-hexamethyldisilazane.

The optionally protected 2'-deoxy-2'-halo-L-arabinonucleoside (11) can then be deprotected, if necessary, by methods well known to those skilled in the art, as taught in Greene, et al., *Protective Groups in Organic Synthesis*, John Wiley and Sons, Second Edition, 1991, to obtain the 2'-deoxy-2'-halo-L-arabinonucleoside (I). The deprotection can be carried out in any appropriate solvent that facilitates the desired result. This reaction can be accomplished at any temperature that allows the reaction to proceed at an acceptable rate without promoting decomposition or excessive side products. For example, acyl protecting groups, and in particular a benzoyl group, can be deprotected with n-butylamine in methanol at reflux.

In cases where compounds are sufficiently basic or acidic to form stable nontoxic acid or base salts, pharmaceutically acceptable salts may be synthesized. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. In particular, examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Any of the nucleosides described herein can be derivatized to its nucleoside or nucleotide prodrug. A number of nucleotide prodrug ligands are known. In general, alkylation, acylation or other lipophilic modification of the mono, di or triphosphate of the nucleoside is well known in the art. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research*, 27 (1995) 1–17. Any of these can be used to functionalize the disclosed nucleosides to achieve a desired prodrug.

The active nucleoside can also be provided as a 5'-phosphoether lipid or a 5'-ether lipid, as disclosed in the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." *AIDS Res. Hum. Retro Viruses*. 6:491–501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." *J. Med. Chem.* 34:1408.1414; Hosteller, K. Y., D. D. Richman, D. A. Carson, L. M. Stuhmiller, G. M. T. van Wijk, and H. van den Bosch. 1992. "Greatly enhanced inhibition of human immunodeficiency virus type 1 replication in CEM and HT4–6C cells by 3'-deoxythymidine diphosphate dimyristoylglycerol, a lipid prodrug of 3,-deoxythymidine." *Antimicrob. Agents Chemother.* 36:2025.2029; Hosetler, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." *J. Biol. Chem.* 265:61127.

Nonlimiting examples of U.S. patents that disclose suitable lipophilic substituents that can be covalently incorporated into the nucleoside, preferably at the 5'-OH position of the nucleoside or lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.), all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

Preparation of 2'-deoxy-2'fluoro-β-L-arabinofuranosyl Thymidine (L-FMAU)

The peracetylated bromosugar of L-arabinose (15, FIG. 1) can be obtained according to literature procedure as a solid, in 57% yield after crystallization from ether (Balog, A.; Yu, M. S.; Curran, D. P. *Synthetic Comm.* 1996, 26, 935). The material is very unstable at room temperature and had to be used immediately or stored in a freezer.

An optionally protected L-arabinal can also be obtained according to a literature procedure in 60% yield after column chromatography (Smiatacz, Z.; Myszka, H. *Carbohydr. Res.* 1988, 172, 171).

The optionally protected L-arabinal can then be fluorinated via addition of SELECTFLOUR™ by a modification of a literature procedure to afford an optionally protected 2-deoxy-2-fluoro-L-arabinopyranose as a syrup in 42% yield (Albert, M.; Dax, K.; Ortner, J. *Tetrahedron* 1998, 54, 4839). Traces of what could possibly be the L-ribo isomer were detected by $^{19}$F-NMR (ratio L-arabino:L-ribo 30:1). The D-isomer of 2-deoxy-2-fluoro-L-arabinopyranose was made by a similar procedure (Albert, M.; Dax, K.; Ortner, J. *Tetrahedron* 1998, 54, 4839). In the reference, nitromethane:water was used as a solvent, which may account. for better yields (68% D-arabino and 7% of the D-ribo isomer). Alternatively, acetone: water can be used, which may account for better selectivity.

Optionally protected 2-deoxy-2-fluoro-L-arabinopyranose can then be deprotected if necessary. For example, deacetylation of 3,4-di-O-acetyl-2-deoxy-2-fluoro-L-arabinopyranose was (17, FIG. 1) can be achieved with NaOMe in methanol in one hour at room temperature. The desired unprotected 2-deoxy-2-fluoro-L-arabinopyranose (18) was obtained as an oil in a 100% yield. $^{1}$H-NMR and $^{13}$C-NMR are coincident with the ones described in the literature for the D-isomer (Bols, M.; Lundt, I. *Acta Chem. Scand.* 1990, 44, 252). The D-isomer of 18 was previously made by three different groups but in a less efficient way.

Treatment of unprotected 2-deoxy-2-fluoro-L-arabinopyranose with one equivalent of either sulfuric or hydrochloric acid at room temperature failed to give the desired furanoside. Only unreacted starting material was detected. Using nine equivalents of hydrochloric acid gave the desired product 2-deoxy-2-fluoro-L-arabinofuranose, which was contaminated with starting material (2:1 ratio). The best result, so far, was achieved by refluxing 2-deoxy-2-fluoro-L-arabinopyranose with 1 equivalent of sulfuric acid in dry methanol. After 6 hours all of the starting material had disappeared affording 2-deoxy-2-fluoro-L-arabinofuranose as an oil in 80% yield. $^{1}$H—, $^{13}$C- and $^{19}$F-NMR indicated a 3:1 α:β mixture of anomers, with some minor impurities. L-ribo- and L-arabinopyranoside as well as L-ribofuranoside are the possible side products. The D-isomer of 2-deoxy-2-fluoro-L-arabinofuranose was previously made by two different groups, but in less efficient ways (Wright, J. A.; Taylor, N. F.; Fox, J. J. *J. Org. Chem* 1969, 34, 2632. and Wysocki, R. J.; Siddiqui, M. A.; Barchi, J. J.; Driscoll, J. S.; Marquez, V. E. *Synthesis* 1991, 1005).

2-Deoxy-2-fluoro-L-arabinofuranose can then be optionally protected. For example, benzoylation of crude 2-deoxy-2-fluoro-L-arabinofuranose gave a mixture that was resolved by flash column chromatography to afford the a furanoside form of 1-O-methyl-2-deoxy-2-fluoro-3,5-di-O-benzoyl-L-arabinofurnaoside (20) as an oil in 44% yield. Other fractions were isolated and have been characterized and the corresponding β-L-arabinofuranoside derivative was detected as the major impurity. The same reaction is described for the D-isomer (*J. Med. Chem.* 1970, 13, 269). They partially describe the D-isomer of 20 optical rotation and CHN, but no spectroscopic data was provided. The absolute value for the optical rotation was similar to the one described for the D-isomer: $[\alpha]_D^{20}$=−98 (c 1.0 EtOH) (lit. value: $[\alpha]_D^{20}$=+108 (c 1.8 EtOH for the D-isomer).

Optionally protected 2-deoxy-2-fluoro-L-arabinofuranose can then be activated, preferably via bromination, and coupled to an optionally protected thymine, such as trimethylsilylthymine, to obtain optionally protected 2'-deoxy-2'-fluoro-L-arabino-furanosyl-thymine. For example, the methyl glycoside (20) can be converted to the intermediate bromosugar (21) under HBr/AcOH condition, which in turn was coupled with silylated thymine (22) under standard conditions affording the known di-O-benzoyl-L-FMAU (23) in 42% crude yield (30% after crystallization from EtOH). The $^{1}$H-NMR was identical to the ones described in the literature for the L- and D-isomers (Du, J.; Choi, Y.; Lee, K.; Chun, B. K.; Hong, J. H.; Chu, C. K. *Nucleosides and Nucleotides* 1999, 18, 187), and to a reference sample (Ma, T.; Pai, S. B.; Zhu, Y. L.; Lin, T. S.; Shanmunganathan, K.; Du, J. F.; Wang, C.-G.; Kim, H.; Newton, G. M.; Cheng, Y.-C.; Chu, C. K. *J. Med. Chem.* 1996, 39, 2835.; and Du, J.; Choi, Y.; Lee, K.; Chun, B. K.; Hong, J. H.; Chu, C. K. *Nucleosides and Nucleotides* 1999, 18, 187; and Tan, C. H.; Brodfuehrer, P. R.; Brundidge, S. P.; Sapino, C.; Howell, H. G. *J. Org. Chem.* 1985, 50, 3647). However, the melting point (160° C.) was identical to the reference sample but differs with the values published in the literature: 120–122° C. for the D-isomer and 118–120° C. for the L-isomer (Tan, C. H.; Brodfuehrer, P. R.; Brundidge, S. P.; Sapino, C.; Howell, H. G. *J. Org. Chem.* 1985, 50, 3647.; and Du, J.; Choi, Y.; Lee, K.; Chun, B. K.; Hong, J. H.; Chu, C. K. *Nucleosides and Nucleotides* 1999, 18, 187).

The optionally protected 2'-deoxy-2'-fluoro-L-arabinofuranosyl-thymine can then be deprotected, if necessary. For examples, di-O-benzoyl-L-FMAU (23) can be debenzoylated with n-butylamine in refluxing methanol reducing the reaction time to 3 hours, from the 24 or 48 hours required when ammonia was used at room temperature (Ma, T.; Pai, S. B.; Zhu, Y. L.; Lin, T. S.; Shanmunganathan, K.; Du, J. F.; Wang, C.-G.; Kim, H.; Newton, G. M.; Cheng, Y.-C.; Chu, C. K. *J. Med. Chem.* 1996, 39, 2835; and Du, J.; Choi, Y.; Lee, K.; Chun, B. K.; Hong, J. H.; Chu, C. K. *Nucleosides and Nucleotides* 1999, 18, 187). Yield of L-FMAU (24) was 77%. Melting point: 188° C. (lit. mp 185–187° C., 184–185° C., 187–188° C.) for the D-isomer; $[\alpha]_D^{20}$=−93 (c 0.25 MeOH) (lit. value: $[\alpha]_D^{20}$=−111 (c 0.23 MeOH), $[\alpha]_D^{20}$=−112 (c 0.23 MeOH)); $^{1}$H-NMR was identical to the ones described in the literature and to a reference sample (Ma, T.; Pai, S. B.; Zhu, Y. L.; Lin, T. S.; Shanmunganathan, K.; Du, J. F.; Wang, C.-G.; Kim, H.; Newton, G. M.; Cheng, Y.-C.; Chu, C. K. *J. Med. Chem.* 1996, 39, 2835; and Du, J.; Choi, Y.; Lee, K.; Chun, B. K.; Hong, J. H.; Chu, C. K. *Nucleosides and Nucleotides* 1999, 18, 187; and Tan, C. H.; Brodfuehrer, P. R.; Brundidge, S. P.; Sapino, C.; Howell, H. G. *J. Org. Chem.* 1985, 50, 3647).

EXAMPLES

Melting points were determined in open capillary tubes on a Gallenkamp MFB-595-010 M apparatus and are uncorrected. The UV absorption spectra were recorded on an Uvikon 931 (KONTRON) spectrophotometer in ethanol. $^{1}$H-NMR spectra were run at room temperature in DMSO-d$_6$ with a Bruker AC 250 or 400 spectrometer. Chemical shifts are given in ppm, DMSO-d$_5$ being set at 2.49 ppm as reference. Deuterium exchange, decoupling experiments or 2D-COSY were performed in order to confirm proton assignments. Signal multiplicities are represented by s (singlet), d (doublet), dd (doublet of doublets), t (triplet), q (quadruplet), br (broad), m (multiplet). All J-values are in Hz. FAB mass spectra were recorded in the positive- (FAB>0) or negative- (FAB<0) ion mode on a JEOL DX 300 mass spectrometer The matrix was 3-nitrobenzyl alcohol (NBA) or a mixture (50:50, v/v) of glycerol and thioglycerol (GT). Specific rotations were measured on a Perkin-Elmer 241 spectropolarimeter (path length 1 cm) and are given in units of $10^{-1}$ deg cm$^2$ g$^{-1}$. Elemental analysis were carried out by the "Service de Microanalyses du CNRS, Division de Vernaison" (France). Analyses indicated by the symbols of the elements or functions were within ±0.4% of theoretical values. Thin layer chromatography was performed on pre-coated aluminum sheets of Silica Gel 60 $F_{254}$ (Merck, Art. 5554), visualization of products being accomplished by UV absorbency followed by charring with 10% ethanolic sulfuric acid and heating. Column chromatography was carried out on Silica Gel 60 (Merck, Art. 9385) at atmospheric pressure.

Example 1

1,2,3,4-tetra-O-acetyl-L-arabinopyranose (14)

To a well stirred suspension of L-arabinose (13) (100 g, 0.67 mol) in dry pyridine (270 mL) at 0° C., was slowly added acetic anhydride (360 mL, 388 g, 3.8 mol.) The suspension was then stirred at room temperature for 4 hours, after which it became a light brown colored solution. Excess pyridine and acetic anhydride were removed by azeotropic evaporation with toluene. Crude (14) was obtained as a clear oil, and was used in the next step without any further purification.

Example 2

1-α-Bromo-2,3,4-tri-O-acetyl-L-arabinopyranose (15)

Crude tetra-O-acetyl-L-arabinopyranose (14) was dissolved in a mixture of 30% wt HBr in AcOH (400 mL, 2.0 mol) and acetic anhydride (8.0 mL). The solution was stirred at room temperature for 36 hours. The reaction mixture was diluted with methylene chloride (400 mL), and successively washed with: water (3×600 mL), saturated $NaHCO_3$ (2×500 mL) and water (3×600 mL), dried, filtered and evaporated to a syrup that was crystallized from ethyl ether to afford (14) (129 g, 0.380 mol, 57% from 13), as a white solid: $^1$H-NMR ($CDCl_3$) δ 6.67 (1H, d, J=3.8, H-1), 5.37 (2H, m) and 5.06 (1H, m) (H-2, H-3 and H-4), 4.18 (1H, d, J=13.3, H-5), 3.91 (1H, dd, J=13.3 and J=1.7, H-5'), 2.13 (3H, s, $CH_3COO$), 2.09 (3H, s, $CH_3COO$), 2.01 (3H, s, $CH_3COO$).

Example 3

3,4-di-O-acetyl-L-arabinal (16)

To a well stirred solution of NaOAc (35 g, 0.43 mol) and AcOH (115 mL) in water (200 mL) at −5° C., was slowly added a solution of $CuSO_4.5H_2O$ (7 g, 28 mmol) in water (23 mL), and then Zn dust (70 g, 0.11 mol) in portions, maintaining the temperature at or below −5° C. To this suspension was added the bromo sugar 15 (34 g, 0.10 mol) in portions and the mixture stirred vigorously for 3 hours at −5° C. and then overnight at room temperature. The mixture was filtered and washed with water (250 mL) and methylene chloride (250 mL). The phases were separated, and the aqueous layer washed with methylene chloride (2×125 mL). The combined organic layers were successively washed with: water (2×250 mL), saturated $NaHCO_3$ (2×1250 mL) and water (2×250 mL), dried, filtered, and evaporated to a colorless syrup (~20 g). The syrup was purified by flash column chromatography (300 g silica gel, hexane:EtOAc 4:1) to afford 16 (12.0 g, 60 mmol, 60%) as a colorless syrup: $^1$H-NMR ($CDCl_3$) δ6.48 (1H,d, J=6.0 H-1), 5.44 (1H, m, H-3), 5.19 (1H, dt, J=4, J=4, J=4, J=9, H-4), 4.83 (1H, dd, J=5, J=6, H-4), 4.00 (2H, m, H-5 and H-5'), 2.08 (3H, s, $CH_3COO$), 2.07 (3H, s $CH_3COO$).

Example 4

3,4-di-O-acetyl-2-deoxy-2-fluoro-L-arabinopyranose (17)

To a well stirred solution of glycal (16) (12.0 g, 60 mmol) in acetone:water (4:2 v:v, 120 mL) was added SELECT-FLUOR™ (26 g, 73 mmol). The solution was stirred overnight at room temperature. The solution was then heated at reflux for 1 hour to complete the reaction. After cooling to room temperature, the acetone was removed in vacuo. Water (150 mL) was added and extracted with EtOAc (3×150 mL). The combined organic fractions were successively washed with: 1N HCl (2×200 mL), and water (2×200 mL) dried, filtered, and evaporated to afford 17 (6.0 g, 25 mmol, 42%) as a syrup: $^{13}$C-NMR ($CDCl_3$ δ 170.35 ($CH_3COO$), 170.27 ($CH_3COO$), 95.01 (C-1α, d, $J_{C-1,F}$=24.5), 90.81 (C-1β, d, $J_{C-1,F}$=21.5), 89.10 (C-2α, d, $J_{C-2,F}$=184.3), 85.85 (C-2βd, $J_{C-2,F}$=188.0), 70.61 (C-3α,d, $J_{C-3,F}$=19.5), 69.57 (C-4β, d, $J_{C-4,F}$=7.7), 68.66 (C-4α, d, $J_{C-4,F}$=8.3), 67.53 (C-3β,d, $J_{C-3,F}$=17.8), 63.90 (C-5α), 60.26 (C-5β), 20.73 ($CH_3COO$), 20.67 ($CH_3COO$), 20.62 ($CH_{C3}COO$), 20.56 ($CH_3COO$).

Anal. Calcd. for $C_9H_{13}O_6F$: C, 45.77; H, 5.55. Found: C, 45.64; H, 5.51.

Example 5

2-deoxy-2-fluoro-L-arabinopyranose (18)

A solution of 17 (5.7 g, 24.1 mmol) in dry methanol (220 mL) was treated with 0.1 N NaOMe in methanol (114 mL, 11.4 mmol) and stirred for 1 hour at room temperature. The solution was then neutralized with DOWEX 50W X8-100, filtered and evaporated to afford 18 (3.7 g, 24 mmol, 100%) as a yellow syrup: $^{13}$C-NMR ($D_2O$) δ 94.19 (C-1α, d, $J_{C-1,F}$=23.0), 92.24 (C-2α, d, $J_{C-2,F}$=179.6), 90.10 (C-1β, d, $J_{C-1,F}$=20.3), 88.60 (C-2β, d, $J_{C-2,F}$=182.3), 70.77 (C-3α, d, $J_{C-3,F}$=18.2), 69.03 (C-4β, d, $J_{C-4,F}$=8.0), 68.90 (C-4α, d, $J_{C-4,F}$=10.2), 66.85 (C-3β, d, $J_{C-3,F}$=18.2), 66.32 (C-5α), 62.21 (C-5β).

Example 6

1-O-methyl-2-deoxy-2-fluoro-L-arabinofuranoside (19)

A solution of 18 (790 mg, 5.2 mmol) and $H_2SO_4$ (60.1 μL, 1.1 mmol) in dry methanol (12.2 mL) was treated at reflux for 6 hours. The reaction was cooled to room temperature, neutralized with DOWEX SBR, filtered and evaporated, to afford 19 (700 mg, 4.21 mmol, 80%) as a syrup: $^{13}$C-NMR ($CD_3OD$) δ 107.48 (C-1α, d, $J_{C-1,F}$=35.6), 103.20 (C-2α, d, $J_{C-2,F}$=178.8), 101.98 (C-1β, d, $J_{C-1,F}$=16.8), 96.80 (C-2β, d $J_{C-2,F}$=199.3), 85.15 (C-4α, d, $J_{C-3,F}$=5.0), 83.69 (C-4β, d, $J_{C-4,F}$=10.7), 76.70 (C-3α, d, $J_{C-4,F}$=27.0), 74.54 (C-3β, d, $J_{C-3,F}$=21.5), 65.00 (C-5β), 62.52 (C-5α). 55.58 ($OCH_3β$), 54.94 ($OCH_3α$).

Example 7

1-O-methyl-2-deoxy-2-fluoro-3,5-di-O-benzoyl-L-arabinofuranoside (20)

To a well stirred solution of 19 (664 mg, 4 mmol) in dry pyridine (10 mL) at 0° C., was slowly added benzoyl chloride (2.5 mL, 3.0 g, 21.5 mmol). After stirring for 30 minutes at 0° C., it was left at room temperature for 3 hours. The reaction was quenched with water (10 mL) and saturated $NaHCO_3$ (30 mL) and stirred for 30 minutes. It was then diluted with methylene chloride (50 mL) and more saturated $NaHCO_3$ (30 mL). The organic layer was separated and successively washed with: saturated $NaHCO_3$ (50 mL), water (2×50 mL), 1N HCl (2×50 mL), water (50 mL), saturated $NaHCO_3$ (50 mL) and water (2×50 mL), dried, filtered and evaporated to a brown syrup (1.9 g), that was purified by flash column chromatography (50 g silica gel, hexane:EtOAc 95:5). A major faction was isolated as a syrup and characterized as 20 (α anomer, 670 mg, 1.79 mmol, 44%): $[α]_D^{20}$=−98 (c 1.0 EtOH) (lit. value: $[α]_D^{20}$=+108 (c 1.8 EtOH) for the D-isomer); ¹H-NMR (CDCl₃) δ 8.20–7.40 (15 H, m, ArH), 5.48 (1H, dd, J=23.1, H-3), 5.21 (1H, d, J=10.6, H-1), 5.11 (1H, d, J=49.2, H-2), 4.76 (1H, dd, J=3.6 and J=12.0, H-5), 4.63 (1H, dd, J=4.4 and J=12.0, H-5'), 3.45 (3H, s, OCH₃); ¹³C-NMR (DCl₃) δ 166.20 (C=O), 165.67 (C=O), 133.57 (Ar), 133.07 (Ar), 129.87 (Ar), 129.76 (Ar), 128.49 (Ar), 128.31 (Ar), 106.22(C-1,d,$J_{C-3,F}$=35.1), 98.20 (C-2, d, $J_{C-2,F}$=182.7), 80.85 (C-4), 77.58 (C-3,d,$J_{C-3,F}$=30.44), 63.62 (C-5), 54.86 (OCH₃).

Anal. Calcd. For C₂OH₁₉O₆F: C, 64.17; H, 5.12. Found: C, 64.14; H, 5.08.

Example 8

1(3,5-di-O-benzoyl-2-deoxy-2-fluoro-β-L-arabinofuranosyl) thymine (23)

To a well stirred solution of 20 (289 mg, 0.75 mmol) in dry methylene chloride (0.56 mL) at 0° C., was slowly added 30% wt HBr in AcOH (0.8 mL, 1.08 g, 0.32 g of HBr, 4.0 mmol). The solution was then stirred at room temperature overnight. The brown-red solution was evaporated under vacuum at or below 40° C. It was then coevaporated with dry benzene (3×3 mL) and then once with dry chloroform (3 mL). Bromosugar 21, a syrup, was redissolved in dry chloroform (2 mL): solution A. At the same time a mixture of thymine (25, 208 mg, 1.65 mmol), ammonium sulfate (19 mg), and 1,1,1,3,3,3-hexamethyldisilazane (798 mg, 1.04 mL, 4.95 mmol) in dry chloroform (7.12 mL) was heated at reflux overnight. The resulting clear solution, (an indication that all the thymine was silylated to form compound 22) was cooled to room temperature: solution B. Solution A was added to solution B and heated at reflux for 4 hours. Water (10 mL) was added, and the mixture stirred for 20 minutes. Chloroform (10 mL) was added, the organic phase separated, washed with water (2×10 mL), dried, filtered and evaporated to a syrup that was purified by flash column chromatography (hexane: EtOAc 1:1). Crude 23 (150 mg, 0.32 mmol, 42%) was obtained as a solid. It was crystallized from EtOH to afford pure 23 (100 mg, 0.22 mmol, 30%) as a white solid: mp 160° C. was identical to an original sample of 23 (lit. value: mp 120–122° C. for the D-isomer and 118–120° C. for the L-isomer); ¹H-NMR (CDCl₃) δ 8.52 (1H, bs, N—H), 8.13–7.43 (10H, m, ArH), 7.36 (1H, q, J=1), C—H thymine, 6.35 (1H, dd, J=3.0 and J=22.2, H-1), 5.64 (1H, dd, J=3.0 and J=18.0, H-3), 5.32 (1H, dd, J=3.0 and J=50.0, H-2), 4.86–4.77 (2H, m, H-5 and H-5'), 4.49 (1H, q, H-4), 1.76 (3H, d, J=1.0, Thymine CH₃).

Example 9

1-(2-deoxy-2-fluoro-β-L-arabinofuranosyl)thymine (24)

A solution of 23 (47 mg, 0.1 mmol) and n-butylamine (0.74 g, 1.0 mL, 10 mmol) in methanol (2 mL) was heated at reflux for 3 hours. The solution was evaporated to dryness and triturated with ethyl ether to afford a solid that was filtered, washed with ether and dried to afford 24 (20 mg, 0.077 mmol, 77% as a white solid: mp 188° C. (lit. value: mp 185–187° C., 184–185° C., 187–188° C. for the D-isomer); $[α]_D^{20}$=−93 (c 0.25 MeOH); (lit. value: $[α]_D^{20}$=−111 (c 0.23 MeOH), $[α]_D^{20}$=−122 (c0.023 MeOH)); ¹H-NMR (DMSO-d₆) δ 11.0 (1H, bs, N—H, 7.58 (1H, s, C—H thymine), 6.09 (1H, dd, J=4.2 and J=15.6, H-1), 5.85 (1H, bs, OH), 5.10 (1H, bs, OH), 5.02 (1H, dt, J-4.0, J−3.8 and J−52.8, H-2), 4.22 (1H, dt, J−3.8, J−4.0 and J=20.3, H-3), 3.76 (1H, q, J=4.0 and J−9.5, H-4), 3.69–3.57 (2H, m, H-5 and H-5'), 1.77 (3H, s, Thymine CH₃).

Many modifications and other embodiments of the invention will be apparent to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included. Although specific terms are employed herein, they are used in a generic and descriptive sense only and not for purposes of limitation.

What is claimed is:

1. A process for the preparation of a 2'-deoxy-2'-halo-β-L-arabinofuranosyl nucleoside of the formula (I):

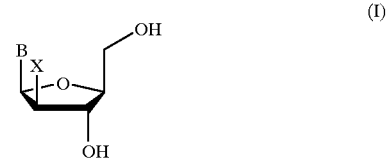

wherein X is a halogen and B is a pyrimidine, purine, heterocyclic or heteroaromatic base which includes the steps of:

(a) halogenating an optionally protected L-arabinal of the formula (III):

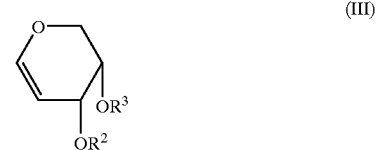

wherein each of R³ is independently hydrogen, alkyl, acyl or silyl and deprotecting, if necessary, to form the 2-deoxy-2-halo-L-arabinopyranose of the formula (II):

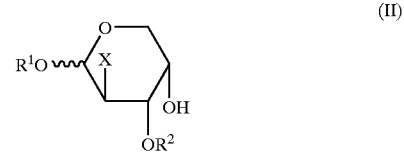

wherein each of R¹ and R² is independently hydrogen, alkyl, acyl or silyl;

(b) converting the 2-deoxy-2-halo-L-arabinopyranose to the 2-deoxy-2-halo-L-arabinofuranose; and (c) coupling the arabinofuranose to a pyrimidine, purine, heterocyclic or heteroaromatic base to form a 2'-deoxy-2'-halo-β-L-arabinofuranosyl nucleoside of the formula (I).

2. A process for the preparation of a 2'-deoxy-2'-halo-β-L-arabinofuranosyl nucleoside of the formula (I):

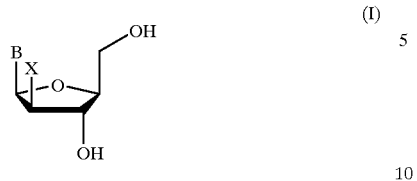
(I)

wherein X is a halogen and B is a pyrimidine, purine, heterocyclic or heteroaromatic base by a process comprising:

(a) halogenating an optionally protected L-arabinose of the formula (IV):

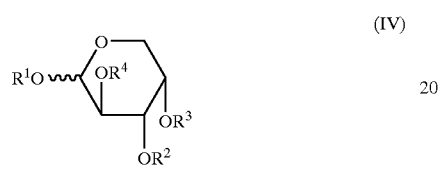
(IV)

wherein each of $R^3$ and $R^4$ is independently hydrogen, alkyl, acyl or silyl by substituting $OR^1$ with a halogen to obtain a compound of the formula (V):

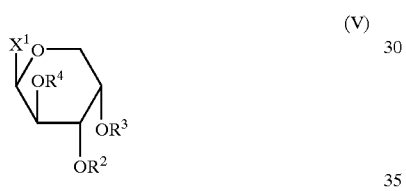
(V)

wherein $X^1$ is a halogen;

(b) reducing the compound of formula (V) to form a compound of formula (III):

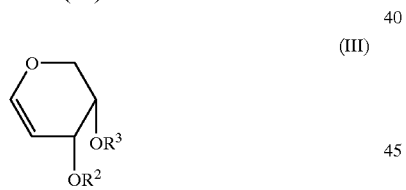
(III)

(c) halogenating the compound of formula (III) and deprotecting if necessary to form a 2-deoxy-2-halo-L-arabinopyranose of the formula (II):

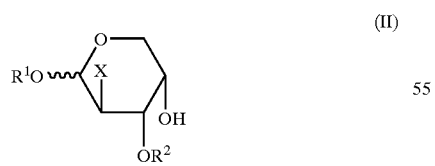
(II)

wherein each of $R^1$ and $R^2$ is independently hydrogen, alkyl, acyl or silyl;

(d) converting the 2-deoxy-2-halo-L-arabinopyranose to the 2-deoxy-2-halo-L-arabinofuranose; and (e) coupling the arabinofuranose to a pyrimidine, purine, heterocyclic or heteroaromatic base to form a 2'-deoxy-2'-halo-β-L-arabinofuranosyl nucleoside of the formula (I).

3. A process for the preparation of a 2'-deoxy-2'-halo-β-L-arabinofuranosyl nucleoside of the formula (I):

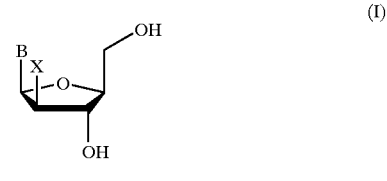
(I)

wherein X is a halogen and B is a pyrimidine, purine, heterocyclic or heteroaromatic base comprising the steps of:

(a) halogenating an optionally protected L-arabinose of the formula (IV):

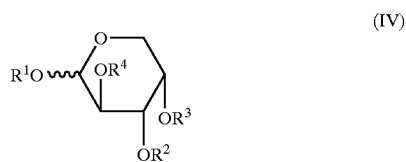
(IV)

wherein each of $R^1$, $R^2$, $R^3$ and $R^4$ is independently hydrogen, alkyl, acyl or silyl by substituting $OR^1$ with a halogen to obtain a compound of the formula (V):

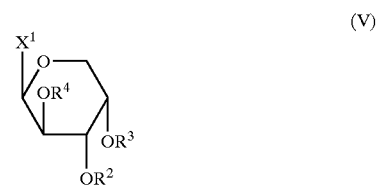
(V)

wherein $X^1$ is a halogen;

(b) reducing the compound of formula (V) to form a compound of formula (III):

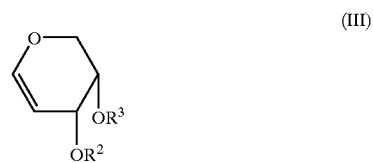
(III)

(c) halogenating the compound of formula (III) and deprotecting if necessary to form the 2-deoxy-2-halo-L-arabinopyranose of the formula (II):

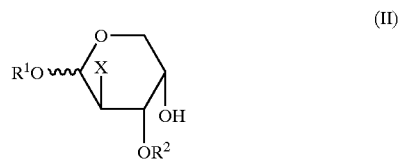
(II)

wherein X is a halogen;

(d) converting the 2-deoxy-2-halo-L-arabinopyranose to a 2-deoxy-2-halo-L-arabinofuranose;

(e) optionally substituting $OR^1$ with O-Acyl or a halogen;

(f) coupling the arabinofuranose to an optionally protected pyrimidine, purine, heterocyclic or heteroaromatic base; and (g) deprotecting, if necessary, to obtain the 2'-deoxy-2'-halo-β-L-arabinofuranosyl nucleoside.

4. A process for the preparation of a 2'-deoxy-2'-fluoro-β-L-arabinofuranosyl thymine (L-FMAU) by preparing a 2-deoxy-2-halo-L-arabinofuranose comprising the steps of:

(a) fluorinating an optionally protected L-arabinal of the formula (III):

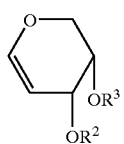

(III)

wherein each $R^3$ is independently hydrogen, alkyl, acyl, or silyl and deprotecting, if necessary, to form the 2-deoxy-2-fluoro-L-arabinopyranose of the formula (II-a):

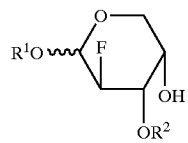

(II-a)

wherein each of $R^1$ and $R^2$ is independently hydrogen, alkyl, acyl, or silyl;

(b) converting the 2-deoxy-2-fluoro-L-arabinopyranose to a 2-deoxy-2-fluoro-L-arabinofuranose; and (c) coupling the arabinofuranose to an optionally protected thymine base to form 2'-deoxy-2'-fluoro-β-L-arabinofuranose thymine.

5. A process for the preparation of 2'-deoxy-2'-fluoro-β-L-arabinofuranose thymine (L-FMAU) by preparing a 2-deoxy-2-halo-L-arabinofuranose comprising the steps of:

(a) halogenating an optionally protected L-arabinose of the formula (IV):

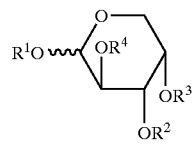

(IV)

wherein each of $R^3$ and $R^4$ is independently hydrogen, alkyl, acyl, or silyl by substituting $OR^1$ with a halogen, to obtain a compound of the formula (V):

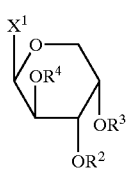

(V)

wherein $X^1$ is a halogen;

(b) reducing the compound of formula (V) to form a compound of formula (III):

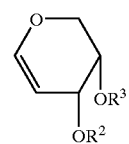

(III)

(c) fluorinating the compound of formula (III) and deprotecting if necessary to form the 2-deoxy-2-fluoro-L-arabinopyranose of the formula (II-a):

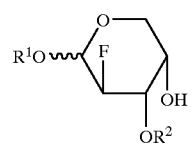

(II-a)

wherein each of $R^1$ and $R^2$ is independently hydrogen, alkyl, acyl, or silyl;

(d) converting the 2-deoxy-2-fluoro-L-arabinopyranose to a 2-deoxy-2-fluoro-L-arabinofuranose; and (e) coupling the arabinofuranose to an optionally protected thymine base to form 2'-deoxy-2'-fluoro-β-L-arabinofuranosyl thymine.

6. A process for the preparation of 2'-deoxy-2'-fluoro-β-L-arabinofuranosyl thymine (L-FMAU) comprising:

(a) halogenating an optionally protected L-arabinose of the formula (IV):

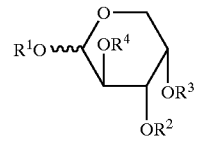

(IV)

wherein each of $R^1$, $R^2$, $R^3$ and $R^4$ is independently hydrogen, alkyl, acyl or silyl by substituting $OR^1$ with a halogen, to obtain a compound of the formula (V):

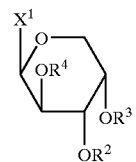

(V)

wherein $X^1$ is a halogen;

(b) reducing the compound of formula (V) to form a compound of formula (III):

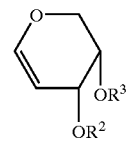

(III)

(c) fluorinating the compound of formula (III) and deprotecting if necessary to form the 2-deoxy-2-fluoro-L-arabinopyranose of the formula (II-a):

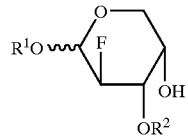
(II-a)

(d) converting the 2-deoxy-2-fluoro-L-arabinopyranose to a 2-deoxy-2-fluoro-L-arabinofuranose;
(e) optionally substituting $OR^1$ with O-Acyl or a halogen;
(f) coupling the arabinofuranose to an optionally protected thymine; and
(g) deprotecting, if necessary, to obtain the 2'-deoxy-2'-fluoro-β-L-arabinofuranosyl thymidine.

7. The process of any one of claims 1–3 or 4–6, wherein the halogenation of the compound of formula (III) is accomplished in nitromethane:water.

8. The process of any one of claims 1–3 or 4–6, wherein the halogenation of the compound of formula (III) is accomplished in acetone:water.

9. The process of any one of claims 1–3 or 4–6, wherein the conversion of the L-arabinopyranose to the L-arabinofuranose is accomplished using one equivalent of sulfuric acid.

10. The process of any one of claims 1–3 or 4–6, wherein the conversion of the L-arabinopyranose to the L-arabinofuranose is accomplished in dry methanol.

11. The process of any one of claims 4–6, wherein the fluorination of the compound of formula (III) is accomplished using (F-TEDA-BF$_4$).

* * * * *